US012725684B2

(12) United States Patent
Onishi et al.

(10) Patent No.: US 12,725,684 B2

(45) Date of Patent: Sep. 1, 2026

(54) INFORMATION PROCESSING SYSTEM, INFORMATION PROCESSING METHOD, AND NON-TRANSITORY COMPUTER READABLE MEDIUM

(71) Applicant: NEC Corporation, Tokyo (JP)

(72) Inventors: Yoshifumi Onishi, Tokyo (JP); Koichi Nihei, Tokyo (JP); Takanori Iwai, Tokyo (JP); Akira Yamauchi, Tokyo (JP); Koichi Kawashima, Tokyo (JP)

(73) Assignee: NEC CORPORATION, Tokyo (JP)

( * ) Notice: Subject to any disclaimer, the term of this patent is extended or adjusted under 35 U.S.C. 154(b) by 95 days.

(21) Appl. No.: 18/713,737

(22) PCT Filed: Dec. 1, 2021

(86) PCT No.: PCT/JP2021/044036

§ 371 (c)(1),
(2) Date: May 28, 2024

(87) PCT Pub. No.: WO2023/100280

PCT Pub. Date: Jun. 8, 2023

(65) Prior Publication Data

US 2025/0029692 A1 Jan. 23, 2025

(51) Int. Cl.
*G16H 10/60* (2018.01)
*G16H 50/20* (2018.01)

(52) U.S. Cl.
CPC ............. *G16H 10/60* (2018.01); *G16H 50/20* (2018.01)

(58) Field of Classification Search
CPC ............................... G16H 10/60; G16H 50/20
See application file for complete search history.

(56) References Cited

U.S. PATENT DOCUMENTS

| | | | | |
|---|---|---|---|---|
| 8,185,623 B2 * | 5/2012 | Lewis | ..................... | G16H 40/20 709/224 |
| 8,751,255 B2 * | 6/2014 | Brown | ..................... | G16H 80/00 705/2 |

(Continued)

FOREIGN PATENT DOCUMENTS

| | | |
|---|---|---|
| JP | 2002-222267 A | 8/2002 |
| JP | 2014-052821 A | 3/2014 |

(Continued)

OTHER PUBLICATIONS

International Search Report for PCT Application No. PCT/JP2021/044036, mailed on Mar. 8, 2022.

(Continued)

*Primary Examiner* — Michael I Ezewoko

(74) *Attorney, Agent, or Firm* — Sughrue Mion, PLLC

(57) ABSTRACT

An information processing system includes: an information acquisition unit that acquires patient information indicating a state of a patient who has visited a first institution or who has been examined by a person associated with the first institution; a determination unit that determines whether or not the patient information satisfies at least one of predetermined determination conditions; and a processing control unit that, when the patient information satisfies at least one of the determination conditions, performs a process for matching a second institution included in setting-origin institutions associated with the satisfied determination condition with the patient. Each of the predetermined determination conditions is a condition for determining whether a suspicion of a predetermined disease is correct or not, and is associated with a setting-origin institution that has set that determination condition.

14 Claims, 19 Drawing Sheets

(56) References Cited

U.S. PATENT DOCUMENTS

| | | | | | |
|---|---|---|---|---|---|
| 11,270,800 | B1 * | 3/2022 | Mitidis | A61B 5/0205 | |
| 11,361,386 | B2 * | 6/2022 | Phillips | G16H 10/60 | |
| 11,657,911 | B2 * | 5/2023 | Guelich | G16H 40/20 | 705/2 |
| 11,862,345 | B2 * | 1/2024 | Ghazaleh | G06F 18/2411 | |
| 2008/0147441 | A1 * | 6/2008 | Kil | G06Q 40/08 | 705/2 |
| 2014/0052465 | A1 * | 2/2014 | Madan | G16Z 99/00 | 705/2 |
| 2014/0249840 | A1 * | 9/2014 | Brown | G06Q 30/0627 | 705/2 |
| 2016/0063212 | A1 * | 3/2016 | Monier | G16H 10/60 | 705/3 |
| 2018/0240545 | A1 * | 8/2018 | Brown | G16H 80/00 | |
| 2020/0152320 | A1 * | 5/2020 | Ghazaleh | G06F 18/23213 | |
| 2020/0160950 | A1 * | 5/2020 | Phillips | G16H 10/60 | |
| 2020/0184402 | A1 * | 6/2020 | Gutman | G06Q 10/06393 | |
| 2020/0243191 | A1 * | 7/2020 | Brown | G06Q 40/08 | |

FOREIGN PATENT DOCUMENTS

| | | | |
|---|---|---|---|
| JP | 2014-089650 | A | 5/2014 |
| JP | 2018-129065 | A | 8/2018 |
| JP | 2020-030728 | A | 2/2020 |
| WO | 2021/005909 | A1 | 1/2021 |

OTHER PUBLICATIONS

JP Office Action for JP Application No. 2023-564332, mailed on Apr. 1, 2025 with English Translation.

* cited by examiner

300
SERVER
N
20-1
FIRST SETTING-ORIGIN HOSPITAL SYSTEM
SETTING-ORIGIN HOSPITAL TERMINAL
200
210
APPOINTMENT SERVER
10
CLINIC SYSTEM
100
CLINIC TERMINAL
110
120
CAMERA
MICRO-PHONE
20-2
SECOND SETTING-ORIGIN HOSPITAL SYSTEM
20-3
THIRD SETTING-ORIGIN HOSPITAL SYSTEM

302

| DETERMI-NATION CONDITION ID | DISEASE ID | DETERMINATION CONDITION | | | SETTING-ORIGIN HOSPITAL ID |
|---|---|---|---|---|---|
| | | FIRST INDIVIDUAL DETERMINATION CONDITION | SECOND INDIVIDUAL DETERMINATION CONDITION | THIRD INDIVIDUAL DETERMINATION CONDITION | |
| C1 | D1 | LOWERED APPETITE | NECK PAIN | — | H1 |
| C2 | D2 | DIZZINESS | NAUSEA | — | H2<br>H3 |
| C3 | D2 | DIZZINESS | STOMACHACHE | LOWERED HEARING ABILITY | H4 |
| C4 | D3 | URIC ACID VALUE IS OUTSIDE REFERENCE RANGE | MEDICATION | PARALYSIS IN BODY | H5 |
| ... | | | | | |

Fig. 5

INFORMATION PROCESSING SYSTEM, INFORMATION PROCESSING METHOD, AND NON-TRANSITORY COMPUTER READABLE MEDIUM

This application is a National Stage Entry of PCT/JP2021/044036 filed on Dec. 1, 2021, the contents of all of which are incorporated herein by reference, in their entirety.

TECHNICAL FIELD

The present disclosure relates to an information processing system, an information processing method, and a non-transitory computer readable medium, and in particular, to an information processing system, an information processing method, and a non-transitory computer readable medium for matching a medical institution with a patient.

BACKGROUND ART

In recent years, telemedical consultation has attracted attention. For example, Patent Literature 1 discloses a server that receives measurement data and inquiry data from an anthropometric apparatus provided in a satellite town or the like, determines a diagnostic institution appropriate for making a diagnosis based on these data, and sends these data to a computer of the diagnostic institution. The server receives data on the diagnostic result from the computer of the diagnostic institution, which has received the aforementioned data, and sends the diagnostic result to the computer of a member who has been diagnosed. In this way, the server carries out telediagnosis.

CITATION LIST

Patent Literature

Patent Literature 1: Japanese Unexamined Patent Application Publication No. 2002-222267

SUMMARY OF INVENTION

Technical Problem

Note that a research institution which conducts clinical research collects data on patients suffering from a disease that the research institution is studying as case data, and uses the collected data to prevent or elucidate the disease, or verify effects of treatments for the disease. Although it is necessary to collect an enormous amount of case data to advance the research, there is a limit to the amount of case data that can be collected by such a research institution. Therefore, it is desired to efficiently recruit (i.e., collect) patients who may have a disease that a medical institution is studying from other medical institutions.

In view of the above-described problem, an object of the present disclosure is to provide an information processing system, an information processing method, and a non-transitory computer readable medium for enabling a research institution which is collecting case data to efficiently collect case data.

Solution to Problem

An information processing system according to an aspect of the present disclosure includes:

information acquisition means for acquiring patient information indicating a state of a patient who has visited a first institution or who has been examined by a person associated with the first institution;

determination means for determining whether or not the patient information satisfies at least one of predetermined determination conditions; and processing control means for, when the patient information satisfies at least one of the determination conditions, performing a process for matching a second institution included in setting-origin institutions associated with the satisfied determination condition with the patient, in which each of the predetermined determination conditions is a condition for determining whether a suspicion of a predetermined disease is correct or not, and is associated with a setting-origin institution that has set that determination condition.

An information processing method according to an aspect of the present disclosure includes:

a process of acquiring patient information indicating a state of a patient who has visited a first institution or who has been examined by a person associated with the first institution;

a process of determining whether or not the patient information satisfies at least one of predetermined determination conditions; and a process of, when the patient information satisfies at least one of the determination conditions, performing a process for matching a second institution included in setting-origin institutions associated with the satisfied determination condition with the patient, in which each of the predetermined determination conditions is a condition for determining whether a suspicion of a predetermined disease is correct or not, and is associated with a setting-origin institution that has set that determination condition.

A non-transitory computer readable medium according to an aspect of the present disclosure stores a program for causing a computer to perform:

a process of acquiring patient information indicating a state of a patient who has visited a first institution or who has been examined by a person associated with the first institution;

a process of determining whether or not the patient information satisfies at least one of predetermined determination conditions; and a process of, when the patient information satisfies at least one of the determination conditions, performing a process for matching a second institution included in setting-origin institutions associated with the satisfied determination condition with the patient.

Each of the predetermined determination conditions is a condition for determining whether a suspicion of a predetermined disease is correct or not, and is associated with a setting-origin institution that has set that determination condition.

Advantageous Effects of Invention

According to the present disclosure, it is possible to provide an information processing system, an information processing method, and a non-transitory computer readable medium for enabling a research institution which is collecting case data to efficiently collect case data.

BRIEF DESCRIPTION OF DRAWINGS

FIG. 5 shows an example of a data structure of a determination condition DB according to the second example embodiment;

EXAMPLE EMBODIMENT

Figure 1:
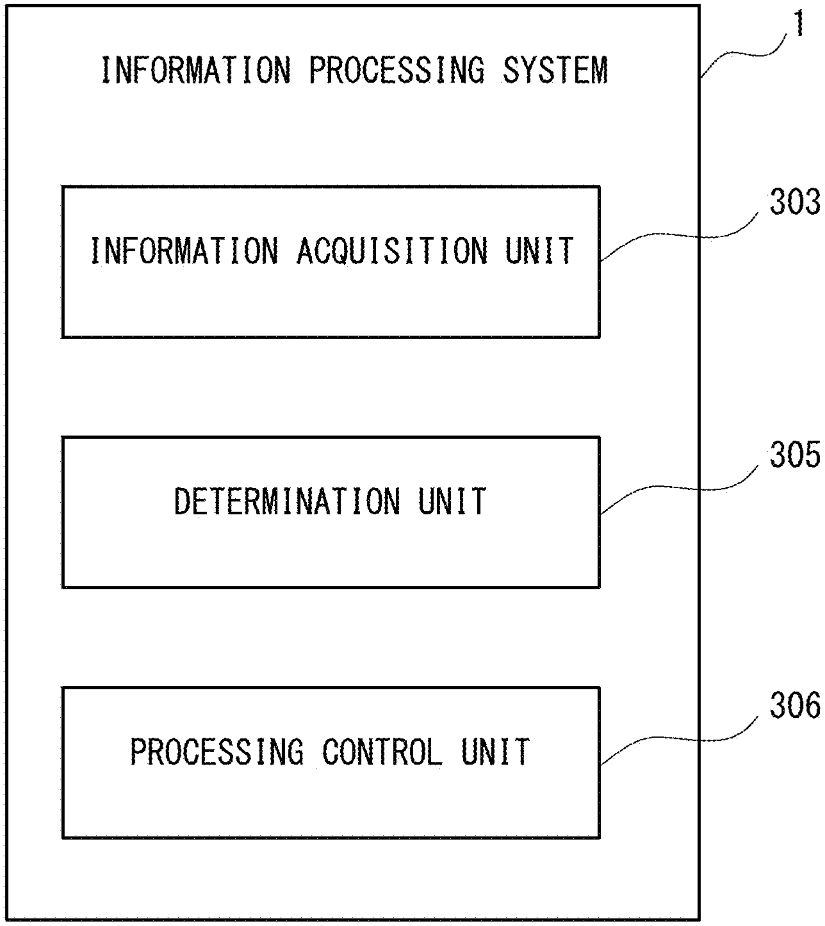
FIG. 1 is a block diagram showing a configuration of an information processing system according to a first example embodiment.

An example embodiment according to the present disclosure will be described hereinafter in detail with reference to the drawings. The same or corresponding elements are assigned the same reference numerals (symbols) throughout the drawings, and redundant descriptions thereof will be omitted as appropriate for clarifying the explanation.

First Example Embodiment

Firstly, a first example embodiment according to the present disclosure will be described. FIG. 1 is a block diagram showing a configuration of an information processing system 1 according to the first example embodiment. The information processing system 1 is a computer system including one computer apparatus or a plurality of computer apparatuses for matching an institution that is collecting case data for a specific disease with a target patient who may have this specific disease.

The aforementioned "institution" to be matched is a hospital, other types of medical institutions or research institutions, a drugstore, or a company that manufactures and sells drugs or medical equipment. The hospital is, for example, a large hospital or a university hospital. The aforementioned "institution" is referred to as a "setting-origin institution" because it sets determination conditions for determining whether a suspicion of a predetermined disease is correct or not. Such determination conditions are categorized or organized in a structured manner by performing statistical processing on case data, or are categorized or organized from case data based on knowledge of experts at the setting-origin institution or research conducted by them. In the following description, "to set (a determination condition)" means to designate the content of the determination condition, for example, to designate determination provisions of the determination condition or designate a parameter such as a threshold for the determination condition. However, "to set (a determination condition)" means instead to select a determination condition from among a plurality of determination conditions the content of each of which have already been designated.

The "target patient" to be matched is a patient who has visited a first institution or has been examined by a person associated with the first institution. To be examined by a person associated with the first institution may mean that a patient is examined by a person associated with the first institution, or a patient present in another place such as his/her home or a simplified clinic (e.g., a mobile clinic) is remotely examined by a person associated with the first institution. The latter may be referred to as a telemedical treatment or an online medical treatment.

The "first institution" is a hospital different from the setting-origin institution. The "first institution" is, for example, a clinic. The person associated with the first institution is a doctor, a nurse, a pharmacist, or other medical staff.

The "examination" is inquiry, an inspection, a palpation, a percussion, an auscultation, or other types of clinical examination.

The information processing system 1 includes an information acquisition unit 303, a determination unit 305, and a processing control unit 306.

The information acquisition unit 303 is also referred to as information acquisition means. The information acquisition unit 303 acquires patient information of the above-described target patient. The "patient information" indicates the state of the patient. In particular, the "patient information" indicates the state of the target patient when he/she visits the first institution or when he/she is examined by a person associated with the first institution. The "state" may be whether there is any of various symptoms such as an appetite, nausea, a body pain, and dizziness, or the degree of morbidity of such symptoms. Further, the "state" may be a test result obtained by a clinical test. Note that the "patient information" may be information about the "state" itself, or may be data, such as video data, audio data, or test data, based on which the "state" is detected.

The determination unit 305 is also referred to as determination means. The determination unit 305 determines whether or not the patient information satisfies at least one of one predetermined determination condition or a plurality of predetermined determination conditions. Note that each of one or a plurality of determination conditions is associated with a setting-origin institution that set that determination condition.

The processing control unit 306 is also referred to as processing control means. When the patient information satisfies at least one determination condition, the processing control unit 306 performs a process for matching a second institution included in setting-origin institutions associated with the satisfied determination condition with the target patient. When there is only one setting-origin institution associated with the satisfied determination condition, the "second institution" is this setting-origin institution. Further, when there is a plurality of setting-origin institutions associated with the satisfied determination condition, the "second institution" may be all the setting-origin institutions or some of the setting-origin institutions. The fact that "there is a plurality of setting-origin institutions" means a case where there is a plurality of satisfied determination conditions or a case where a plurality of setting-origin institutions is associated with one satisfied determination condition. The "process for matching" is also referred to as a matching process. The matching process may be, but is not limited to, notifying a terminal of the first institution of information about the second institution and causing the first institution to output the information about the second institution, transmitting patient information to a terminal of the second institution, or making an appointment for a medical consultation at the second institution for the target patient. Note that by causing the terminal of the first institution to output the information about the second institution, a person associated with the first institution can carry out an operation for preparing a letter of introduction addressed to the setting-origin institution or transmitting the patient information from the terminal of the first institution to a terminal of the setting-origin institution. In this way, it is possible to match the setting-origin institution with the target patient. Note that in the following description, "to output" may be to display an image or the like or to output a sound or voice.

Figure 2:
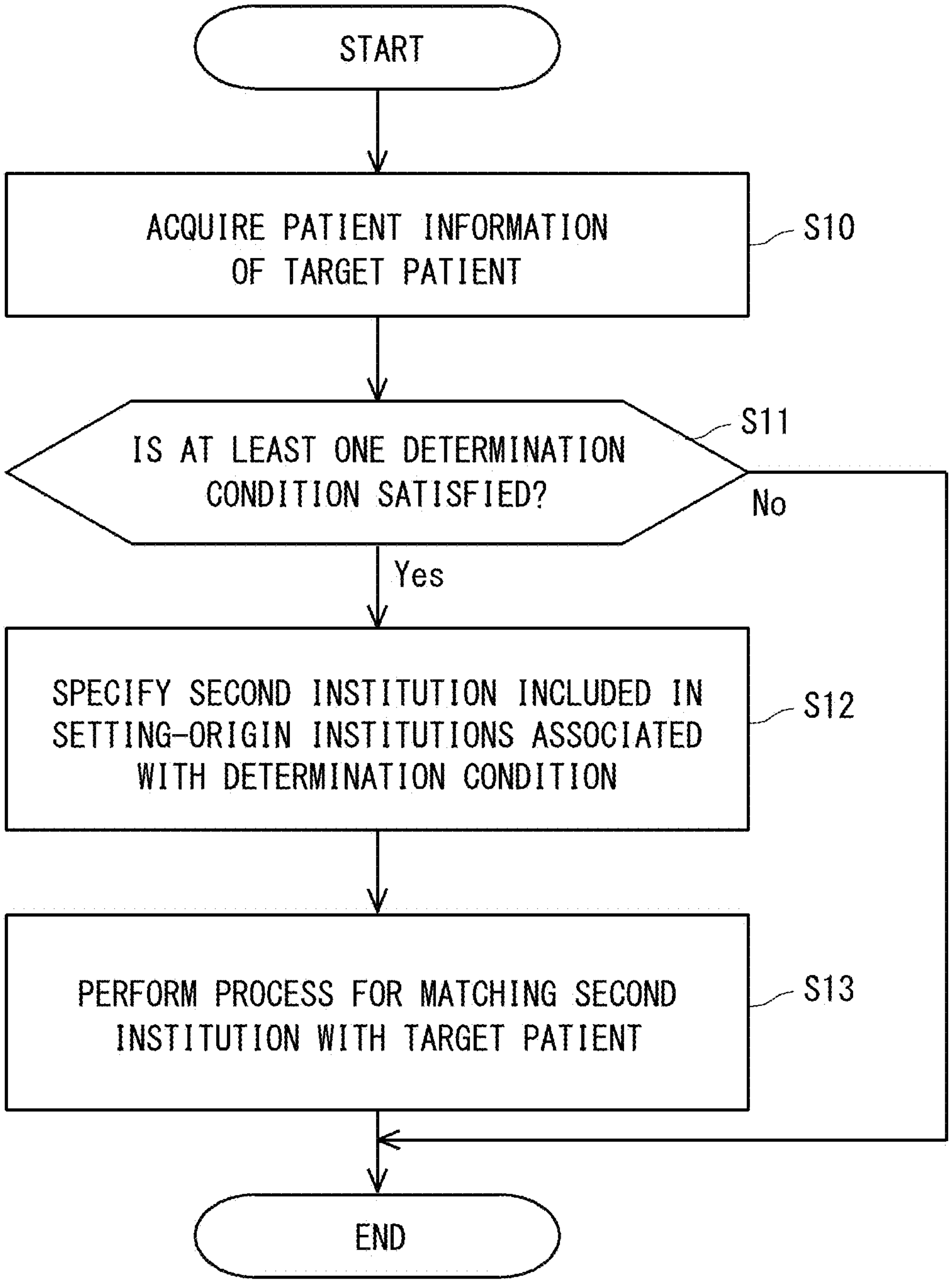
FIG. 2 is a flowchart showing a flow of an information processing method according to the first example embodiment.

FIG. 2 is a flowchart showing a flow of an information processing method according to the first example embodiment. Firstly, the information acquisition unit 303 of the information processing system 1 acquires patient information of a target patient (S10). Next, the determination unit 305 determines whether or not at least one of one or a plurality of predetermined determination conditions is satisfied (S11). When the determination unit 305 does not determine that any of determination conditions is satisfied (No in S11), it finishes the series of processes. On the other hand, when the determination unit 305 determines that at least one determination condition is satisfied (Yes in S11), it specifies setting-origin institutions associated with the satisfied determination condition and specifies a second institution included in the specified setting-origin institutions (S12). Then, the processing control unit 306 performs a process for matching the second institution with the target patient (S13), and finishes the series of processes.

As described above, according to the first example embodiment, the information processing system 1 can remotely match a setting-origin institution which is collecting case data for a specific disease with a target patient. The setting-origin hospital can collect case data to be studied without being geographically restricted or while preventing necessary labor from increasing, i.e., can efficiently collect case data to be studied. Meanwhile, a patient has an opportunity to be treated in or transferred to a setting-origin institution where there is a specialist in a suspected disease just by visiting a first institution or having a medical examination in a first institution.

Second Example Embodiment

Figure 3:
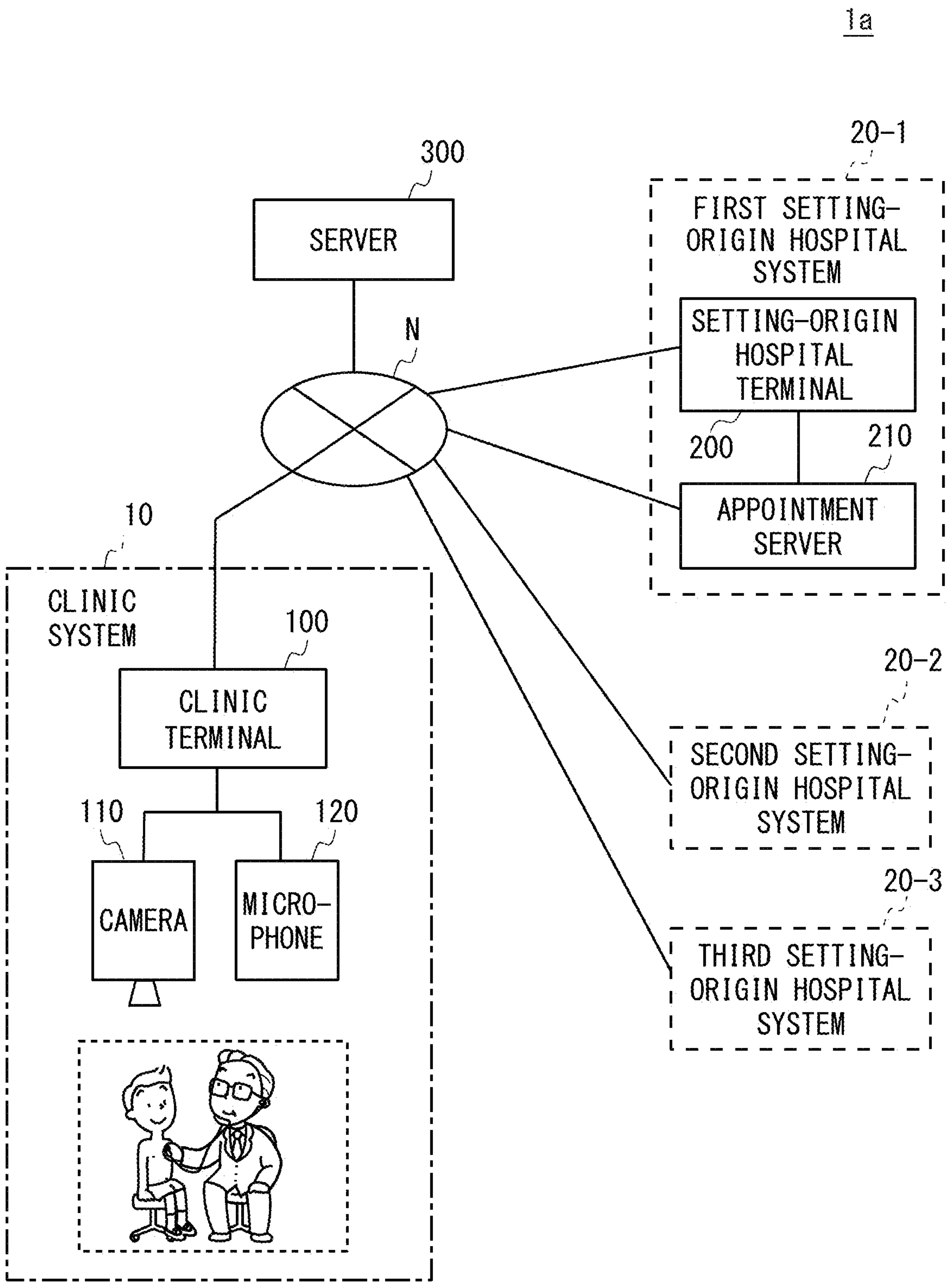
FIG. 3 is a block diagram showing an overall configuration of an information processing system according to a second example embodiment.

Next, a second example embodiment according to the present disclosure will be described. FIG. 3 is a block diagram showing an overall configuration of an information processing system 1*a* according to the second example embodiment. The information processing system 1*a* is an example of the above-described information processing system 1. Note that in the second example embodiment, as an example, the "setting-origin institution" is a large hospital and referred to as the setting-origin hospital, and the "first institution" is a clinic. Further, as an example, the person associated with the setting-origin hospital is a doctor belonging to the setting-origin hospital, and the person associated with the clinic is a doctor belonging to the clinic. A target patient visits the clinic and has a medical examination there.

The information processing system 1*a* includes a clinic system 10, a plurality of setting-origin hospital systems 20-1, 20-2 and 20-3 provided in a plurality of setting-origin hospitals, respectively, and an information processing apparatus (hereinafter referred to as a server) 300. Each of the apparatuses and systems is connected to a wired or wireless network N. Note that the number of setting-origin hospital systems 20 is not limited to three.

(Clinic System 10)

The clinic system 10 is a computer system in the clinic. The clinic system 10 acquires patient information of a target patient who has visited the clinic or a target patient who has been examined by a person associated with the clinic. Then, the clinic system 10 transmits the acquired patient information to the server 300 through the network N.

Specifically, the clinic system 10 includes a clinic terminal 100, a camera 110, and a microphone 120.

The camera 110 and the microphone 120 are disposed in the clinic. For example, the camera 110 and the microphone 120 are installed in a consultation room of the clinic. In this case, as an example, the camera 110 photographs (or films) the target patient who is being questioned by the doctor of the clinic, and the microphone 120 collects voices of the target patient who is being questioned. Further, for example, the camera 110 and the microphone 120 may be installed in an examination room of the clinic. In this case, as an example, the camera 110 photographs (or films) the target patient who is being examined, and the microphone 120 collects voices of the target patient who is being examined. Further, for example, the camera 110 and the microphone 120 may be installed in a waiting room of the clinic. In this case, as an example, the camera 110 and the microphone 120 photograph (or filming) the target patient who is waiting in the waiting room, and the microphone 120 collects voices of the target patient waiting in the waiting room.

The camera 110 and the microphone 120 are connected to the clinic terminal 100, and transmit video data and audio data, respectively, to the clinic terminal 100. The video data and audio data may be collectively referred to as media data.

The clinic terminal 100 is an information terminal provided in the clinic or an information terminal managed by a doctor or other relevant persons of the clinic. The clinic terminal 100 is connected to the network N. The clinic terminal 100 transmits media data acquired from the camera 110 and the microphone 120 to the server 300 through the network N.

Further, when the clinic terminal 100 receives information about a setting-origin hospital from the server 300, it outputs the received information. In this way, the clinic terminal 100 informs the doctor of the clinic of the presence of the hospital which is collecting case data of the target patient.

(Setting-Origin Hospital System 20)

Each of the setting-origin hospital systems 20 is a computer system in the setting-origin hospital. The setting-origin hospital system 20 receives, from the doctor of the setting-origin hospital, designation of a determination condition for a disease for which they are collecting case data from. Then, the setting-origin hospital system 20 transmits a setting request for setting information about the designated determination condition to the server 300 through the network N.

Specifically, the setting-origin hospital system 20 includes a setting-origin hospital terminal 200 and an appointment server 210.

The setting-origin hospital terminal 200 is an information terminal provided in the setting-origin hospital or an information terminal managed by a doctor or other associated persons of the setting-origin hospital. The setting-origin hospital terminal 200 is connected to the network N. The setting-origin hospital terminal 200 receives the content of the determination condition from the doctor of the setting-origin hospital, and transmits a setting request for the designated determination condition to the server 300 through the network N.

The appointment server 210 is a server that receives an appointment for a medical consultation at the setting-origin hospital and manages an appointment status. The appointment server 210 may be connected to the setting-origin hospital terminal 200 and may be configured so as to be able to output the appointment status to the setting-origin hospital terminal 200. Note that the appointment server 210 is not essential in the second example embodiment.

(Server 300)

The server 300 is a computer apparatus that matches a setting-origin hospital with a target patient. The server 300 registers a determination condition included in a setting request received by the setting-origin hospital system 20 in association with the setting-origin hospital. Further, when patient information based on media data received from the clinic system 10 satisfies any of already-registered determination conditions, the server 300 performs a process for matching the setting-origin hospital corresponding to the satisfied determination condition with the target patient.

Figure 4:
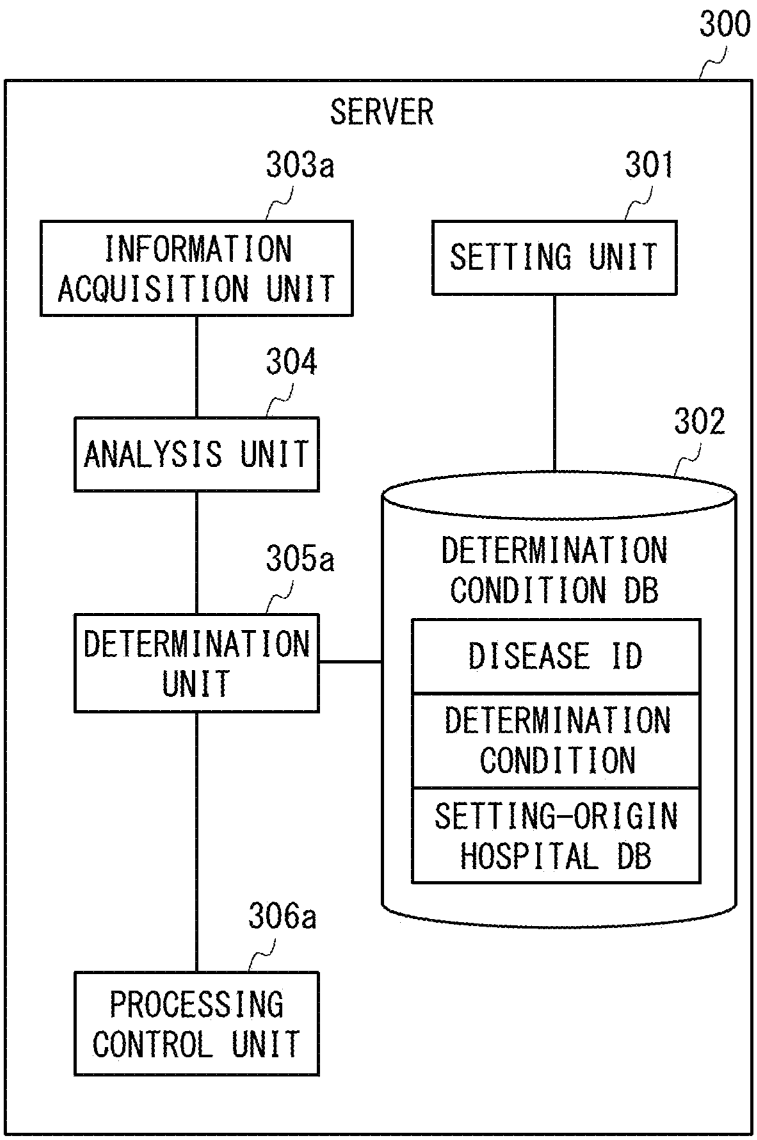
FIG. 4 is a block diagram showing a configuration of a server according to the second example embodiment.

FIG. 4 is a block diagram showing a configuration of the server 300 according to the second example embodiment. The server 300 includes a setting unit 301, a determination condition database (DB) 302, an information acquisition unit 303*a*, an analysis unit 304, a determination unit 305*a*, and a processing control unit 306*a*.

The setting unit 301 is also referred to as setting means. When the setting unit 301 receives a setting request for a designated determination condition from the setting-origin hospital terminal 200, it registers a determination condition included in the setting request in association with a disease ID for identifying a disease that is a determination target of the determination condition and a setting-origin hospital ID. In this way, the determination condition is set. The disease ID may be the name or an identification number of the disease. The setting-origin hospital ID is information for identifying the setting-origin hospital, and may be the name or an identification number of the setting-origin hospital, or the name or an identification number of a doctor of the setting-origin hospital.

Note that the setting-origin hospital ID is associated with setting-origin hospital information which is information about the setting-origin hospital. The setting-origin hospital information may include the name of the setting-origin hospital, the address of the setting-origin hospital, the type of the clinical department, the name of the medical corporation, the size of the setting-origin hospital, the consultation hours, the telephone number, the name or personal history of a doctor belonging to the setting-origin hospital, or information about the disease for which the setting-origin hospital is collecting case data. Therefore, by the above-described setting process performed by the setting unit 301, each determination condition is registered in association with setting-origin hospital information about a setting-origin hospital which has set that determination condition.

Further, when it is found that a determination result is incorrect, the setting unit 301 may update the determination condition. The situation in which it is found that a determination result is incorrect may be a situation in which an incorrect notification is received from the setting-origin hospital terminal 200 or an update request is received from the setting-origin hospital terminal 200. For example, when the setting unit 301 receives an incorrect notification, it may update a parameter such as a threshold for a determination condition. Further, for example, the setting unit 301 may update a determination condition based on update information included in an update request received from the setting-origin hospital terminal 200. In this way, the accuracy of the determination can be improved.

The determination condition DB 302 is a storage device in which determination conditions and the like are stored. In the second example embodiment, disease IDs, determination conditions, and setting-origin hospital IDs are stored in association with each other in the determination condition DB 302. A more detailed data structure of the determination condition DB 302 is shown in FIG. 5.

FIG. 5 shows an example of a data structure of the determination condition DB 302 according to the second example embodiment. In FIG. 5, in the determination condition DB 302, for each determination condition ID, a disease ID, a determination condition, and a setting-origin hospital ID are stored in association with each. Note that the determination condition may be a combination of individual determination conditions. The individual determination condition is a condition related to some of determination provisions in the determination condition, and is a condition used to determine, for each of determination provisions such as an appetite, a fever, diarrhea, dizziness, and a body pain, whether or not the state of the target patient corresponds to a state corresponding to that determination provision. When all the individual determination conditions constituting the same determination condition are satisfied, it is determined that the determination condition is satisfied. This determination is referred to as a matching determination. The order in which individual determination conditions are determined may be determined in advance or may be random.

For example, a determination condition "C1" is a determination condition for determining whether a disease "D1" is suspected. The determination condition "C1" is formed by a combination of an individual determination condition for an appetite and an individual determination condition for a neck pain, and these conditions are set by a setting-origin hospital "H1". According to the determination condition "C1", when the appetite has decreased and the patient feels a neck pain, it is determined that the patient is suspected to have a disease represented by a disease ID "D1".

Note that a plurality of setting-origin hospitals can set the same determination condition. For example, a determination condition "C2" is set by setting-origin hospitals "H2" and "H3".

Further, the individual determination condition may include a determination condition for determining whether a test value is within a reference range or whether a predetermined treatment or medication has been carried out or administered.

For example, a determination condition "C4" is formed by a combination of a first individual determination condition related to a uric acid value, a second individual determination condition related to whether medication has been administered, and a third individual determination condition related to a paralysis of the body. As an example, regarding the determination condition "C4", when the uric acid value was outside a predetermined reference range, and hence medication has been administered for this outside uric acid value, but as a result, a symptom of a paralysis of the body has occurred, a matching determination is made.

The description will be continued by referring to FIG. 4 again. The information acquisition unit 303*a* and the analysis unit 304 are examples of the above-described information acquisition unit 303. The information acquisition unit 303*a* acquires media data from the clinic terminal 100 through the network N. The media data are composed of audio data and video data at the time of a medical consultation or examination by a doctor of the clinic, especially at the time of inquiry. The information acquisition unit 303*a* transmits the acquired media data to the analysis unit 304.

The analysis unit 304 is also referred to as analysis means. The analysis unit 304 generates state analysis information by analyzing the state of the target patient based on the media data. The state analysis information contains information indicating the state of the target patient, which is the analysis result. That is, the state analysis information is information detected from the movement or voices of the target patient.

For example, the analysis unit 304 detects a state that the target patient has a neck pain from video data in which the target patient puts his/her hand on his/her neck. Note that whether the person shown in the video image is the target patient or not may be determined by having the analysis unit 304 perform face authentication.

Further, for example, the analysis unit 304 detects a state that the target patient has a neck pain from audio data in which the target patient has told "Recently, my neck hurts". Note that whether the person who has spoken is the target patient or not may be determined by having the analysis unit 304 perform a voiceprint analysis.

Further, the analysis unit 304 may detect a state that the target patient has a neck pain from a combination of video data and audio data. For example, the analysis unit 304 may recognize a state that the patient has a neck pain from video data in which the target patient has puts his/her hand on his/her neck and audio data in which the target patient has said "It hurts . . . ".

Then, the analysis unit 304 generates patient information containing the state analysis information. The patient information may be state analysis information itself or may include, in addition to the state analysis information, medical record information which is information described in a medical record. The medical record information may be a medical examination result entered by a doctor and may include a special feature at the time of inquiry, a test result, or a treatment status such as medication. The medical record information may be acquired from the clinic terminal 100 through the network N. Then, the analysis unit 304 supplies the patient information of the target patient to the determination unit 305*a*.

The determination unit 305*a* is an example of the above-described determination unit 305. When the patient information satisfies any of determination conditions registered in the determination condition DB 302, the determination unit 305*a* outputs a matching determination for the satisfied determination condition. Then, the determination unit 305*a* refers to the determination condition DB 302 and thereby specifies the setting-origin hospital corresponding to the satisfied determination condition.

The processing control unit 306*a* is an example of the above-described processing control unit 306. The processing control unit 306*a* specifies the specified setting-origin hospital as a second institution.

Note that when there is a plurality of specified setting-origin hospitals, the processing control unit 306*a* may select one of the plurality of setting-origin institutions as the second institution. In this process, the processing control unit 306*a* may select the second institution based on registration information related to at least one of the target patient, the clinic, and the setting-origin hospital.

The registration information related to the target patient may be acquired from a user terminal (not shown) used by the target patient, and may be registered in advance in a registration DB (not shown) by the server 300. Examples of the registration information related to the target patient include attribute information of the target patient, such as an age and a gender of the target patient, the address of his/her home, contact information, and the name of a hospital or the like he/she usually uses. Further, the registration information related to the target patient may include information about a request of the patient, such as a request for a veteran doctor.

The registration information related to the clinic may be acquired from the clinic terminal 100 and registered in the registration DB in advance by the server 300. Examples of the registration information related to the clinic include the address of the clinic and the name of a hospital with which the clinic is affiliated.

The registration information related to the setting-origin hospital may be acquired from the setting-origin hospital terminal 200 of the setting-origin hospital and registered in the registration DB in advance by the server 300. The registration information related to the setting-origin hospital may be setting-origin hospital information of the setting-origin hospital. Further, the registration information related to the setting-origin hospital may include the urgency of case data and the progress of the collection of case data.

In this way, the processing control unit 306*a* can select a setting-origin hospital close to the house or the clinic of the target patient as the second institution. Further, the processing control unit 306*a* can select a setting-origin hospital according to the request of the target patient as the second institution. Further, the processing control unit 306*a* can preferentially select, as the second institution, an urgent setting-origin hospital or a setting-origin hospital in which not many case data are collected.

Then, the processing control unit 306*a* notifies the clinic terminal 100 of the setting-origin hospital information related to the second institution, and causes the clinic terminal 100 to output the setting-origin hospital information. Then, as a matching process, the processing control unit 306*a* supports a doctor of the clinic to prepare a letter of introduction addressed to the second institution. The support for the preparation may be to output a message urging the doctor to prepare a letter of introduction or to output a prescribed form for a letter of introduction. The support for the preparation may be provided when the consent by the patient is obtained.

Figure 6:
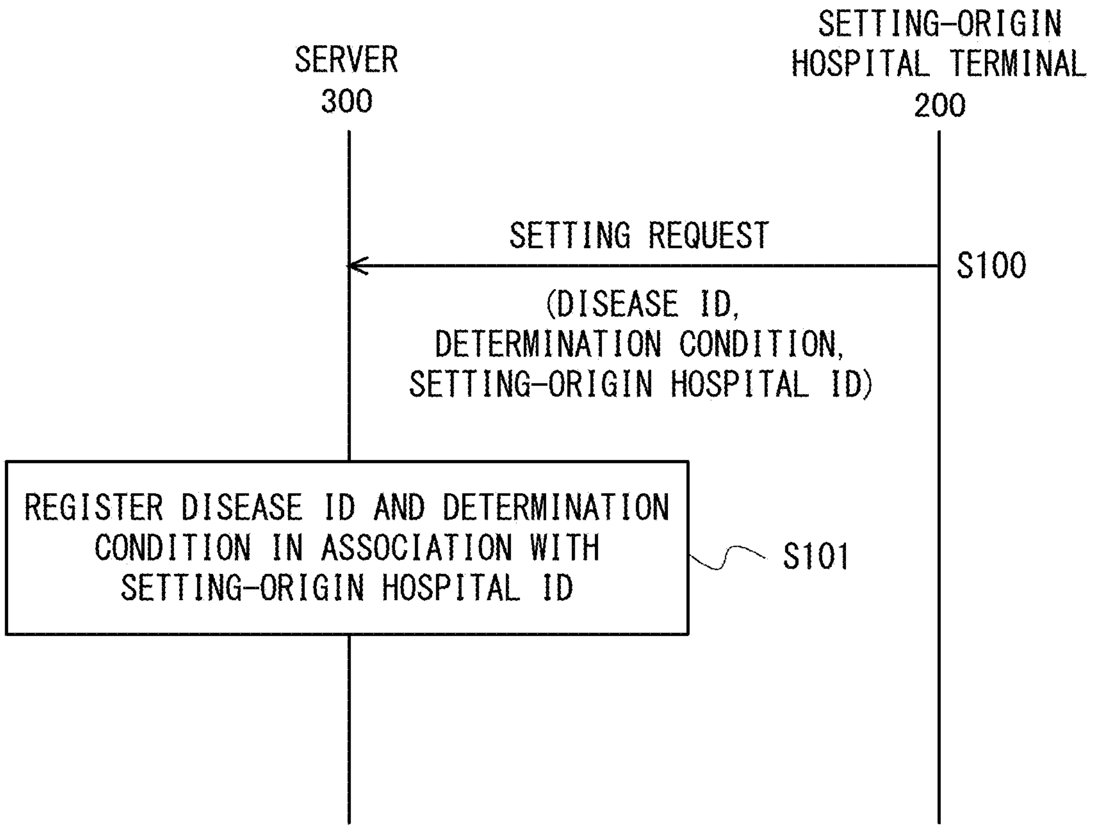
FIG. 6 is a flowchart showing a flow of a process for setting a determination condition according to the second example embodiment.

FIG. 6 is a flowchart showing a flow of a process for setting a determination condition according to the second example embodiment. Firstly, the setting-origin hospital terminal 200 transmits a setting request to the server 300 (S100). For example, the setting request includes a disease ID, a determination condition, and a setting-origin hospital ID. Next, the setting unit 301 of the server 300 registers the disease ID and the determination condition included in the setting request in the determination condition DB 302 in association with the setting-origin hospital ID included in the setting request (S101).

Figure 7:
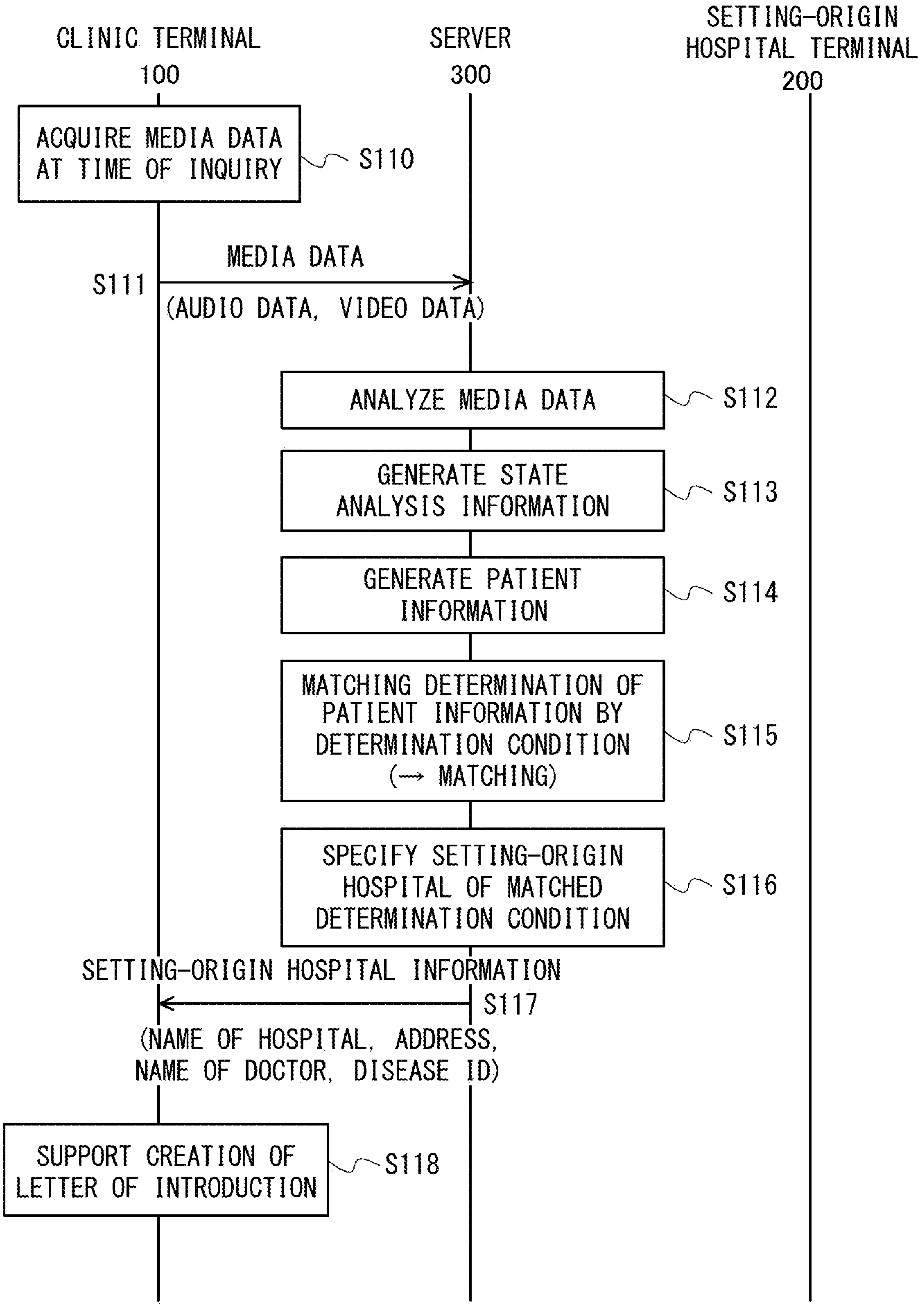
FIG. 7 is a sequence diagram showing an example of a flow of a matching process according to the second example embodiment.

FIG. 7 is a sequence diagram showing an example of a flow of a matching process according to the second example embodiment. In FIG. 7, the media data are composed of video data and audio data at the time when a doctor or the like inquired of the target patient. Firstly, the clinic terminal 100 acquires media data at the time of the inquiry from the camera 110 and the microphone 120 (S110). Then, the clinic terminal 100 transmits the acquired media data to the server 300 (S111). In this way, the information acquisition unit 303*a* of the server 300 acquires the media data.

Next, the analysis unit 304 of the server 300 analyzes the media data (S112) and generates state analysis information based on the media data (S113). Then, the analysis unit 304 generates patient information containing the state analysis information (S114). For example, when the server 300 has already acquired medical record information, the analysis unit 304 generates patient information containing the state analysis information and the medical record information. Next, the determination unit 305*a* determines whether or not there is, among determination conditions registered in the determination condition DB 302, a determination condition that the patient information of the target patient satisfies (S115). Next, the processing control unit 306*a* specifies a setting-origin hospital corresponding to the matched determination condition and regards this specified setting-origin hospital as a second institution (S116). Next, the processing control unit 306*a* transmits setting-origin hospital information associated with the setting-origin hospital ID of the second institution to the clinic terminal 100 (S117). The setting-origin hospital information may include the name of the hospital, an address, the name of a doctor, and a disease ID.

Upon receiving the setting-origin hospital information, the clinic terminal 100, automatically or based on an operation performed by the doctor of the clinic after the setting-origin hospital information is output, provides a support for the preparation of a letter of introduction (S118).

Figure 8:
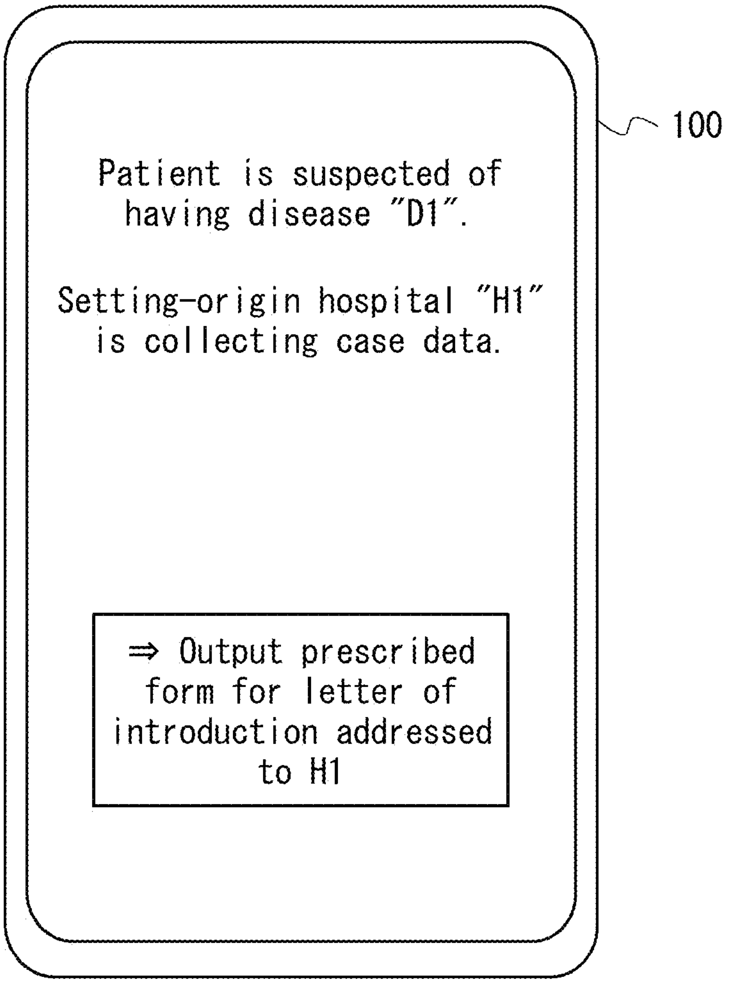
FIG. 8 shows an example of an image displayed on a clinic terminal according to the second example embodiment.

The display screen of the clinic terminal 100 in this case is shown in FIG. 8. FIG. 8 shows an example of an image displayed on the clinic terminal 100 according to the second example embodiment. For example, the fact that the target patient is suspected of having a disease "D1", and that a setting-origin hospital "H1" is collecting case data is displayed on the display unit of the clinic terminal 100. Further, an operation area for outputting a prescribed form for a letter of introduction addressed to the setting-origin hospital "H1" may be displayed on the display unit of the clinic terminal 100. The person associated with the clinic may operate this operation area and output the prescribed form when he/she obtains the consent from the target patient.

As described above, according to the second example embodiment, the server 300 can remotely match a setting-origin institution which is collecting case data for a specific disease with a target patient. The setting-origin hospital can collect case data to be studied without being geographically restricted or while preventing necessary labor from increasing, i.e., can efficiently collect case data to be studied. Meanwhile, a target patient has an opportunity to be treated in or transferred to a setting-origin hospital where there is a specialist in a suspected disease just by visiting a clinic or having a medical examination in a clinic.

Further, in the second example embodiment, the server 300 uses patient information generated based on audio data or video data of the target patient at the time when he/she visits a clinic or is examined there for the determination process. Therefore, the server 300 can include a small abnormality of the target patient, which cannot be directly obtained from the medical record, in the patient information. In this way, the server 300 can perform the determination process based on the small abnormality of the target patient.

First Modified Example of Second Example Embodiment

The matching process may be to provide patient information to the setting-origin hospital terminal 200 instead of or in addition to the support for the preparation of a letter of introduction. That is, the processing control unit 306*a* of the server 300 transmits patient information to the setting-origin hospital terminal 200 when at least one determination condition is satisfied.

Figure 9:
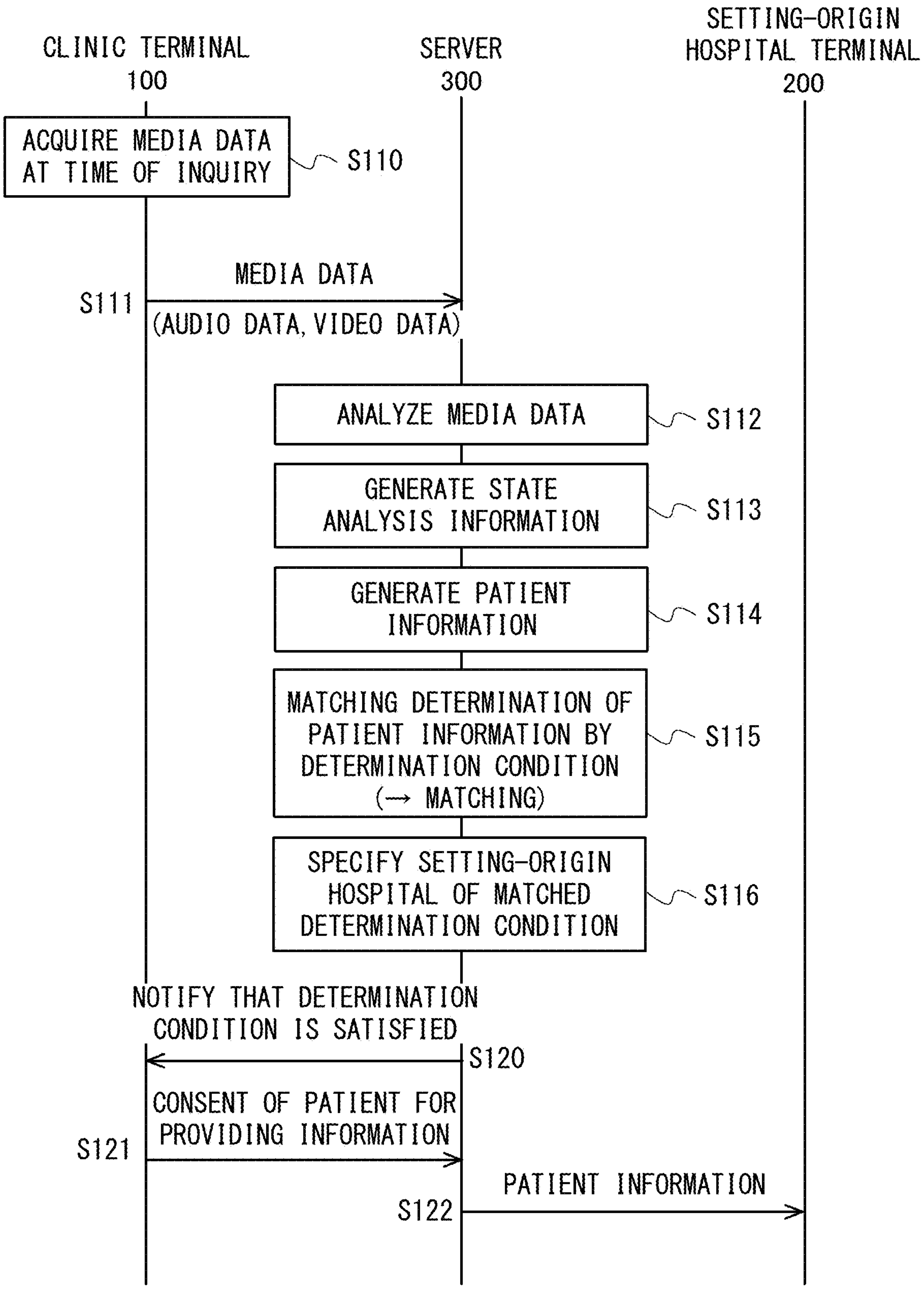
FIG. 9 is a sequence diagram showing a flow of a matching process according to a first modified example of the second example embodiment.

FIG. 9 is a sequence diagram showing a flow of a matching process according to a first modified example of the second example embodiment. The steps shown in FIG. 9 include steps S120 to S122 instead of the steps S117 to S118 shown in FIG. 7.

In the step S120, the processing control unit 306*a* of the server 300 notifies the clinic terminal 100 that the patient information of the target patient satisfies a determination condition. The clinic terminal 100 notifies the server 300 to that effect when the consent from the target patient for providing the information is obtained (S121). The above-described consent from the target patient may be obtained in advance. Then, the processing control unit 306*a* of the server 300 transmits the patient information of the target patient to the setting-origin hospital terminal 200 of the second institution (S122).

Note that the acquisition of the consent from the target patient is not essential, and the processes in the steps S120 and S121 may be omitted. Further, when the processing control unit 306*a* transmits the patient information of the target patient, it may transmit private information (e.g., attribute information) of the target patient to the setting-origin hospital terminal 200 of the second institution, but the private information may be withheld (or concealed) to ensure the privacy of the target patient.

Further, when the target patient has used a plurality of different hospitals for the same symptom, i.e., is sent around from one hospital to another, the processing control unit 306*a* of the server 300 may transmit information indicating this fact together with the patient information of the target patient to the setting-origin hospital terminal 200 of the second institution. In this way, it is possible to convey information about the specialty of the symptom of the target patient or the necessity of a medical consultation or examination by a specialist to the setting-origin hospital terminal 200. Further, it is possible to reduce the psychological burden of the target patient.

Figure 10:
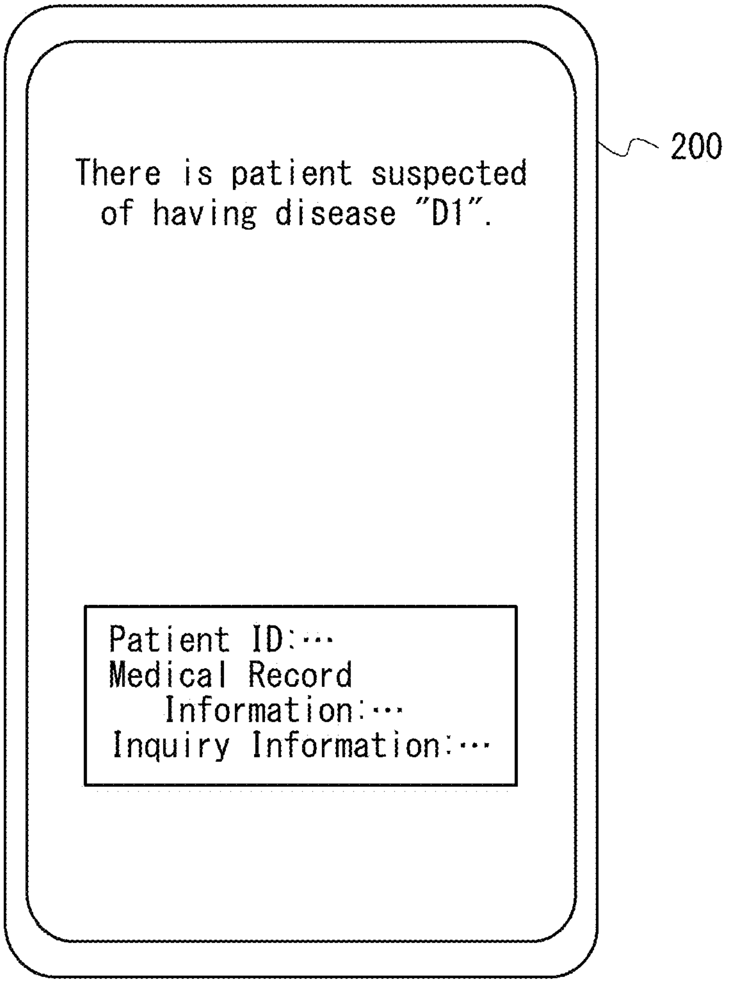
FIG. 10 shows an example of an image displayed on a setting-origin hospital terminal according to the first modified example of the second example embodiment.

FIG. 10 shows an example of an image displayed on the setting-origin hospital terminal 200 according to the first modified example of the second example embodiment. The fact that there is a patient suspected of having a disease "D1", and as the patient information, information about a medical record and inquiry are displayed on the display unit of the setting-origin hospital terminal 200 which has received the patient information.

Second Modified Example of Second Example Embodiment

The matching process may be to support a patient or the like to make an appointment at a setting-origin hospital instead of or in addition to the support for the preparation of a letter of introduction. For example, when at least one determination condition is satisfied, the processing control unit 306*a* of the server 300 accesses an appointment server 210 of the setting-origin hospital and transmit an appointment request for a medical consultation or examination to the appointment server 210.

Figure 11:
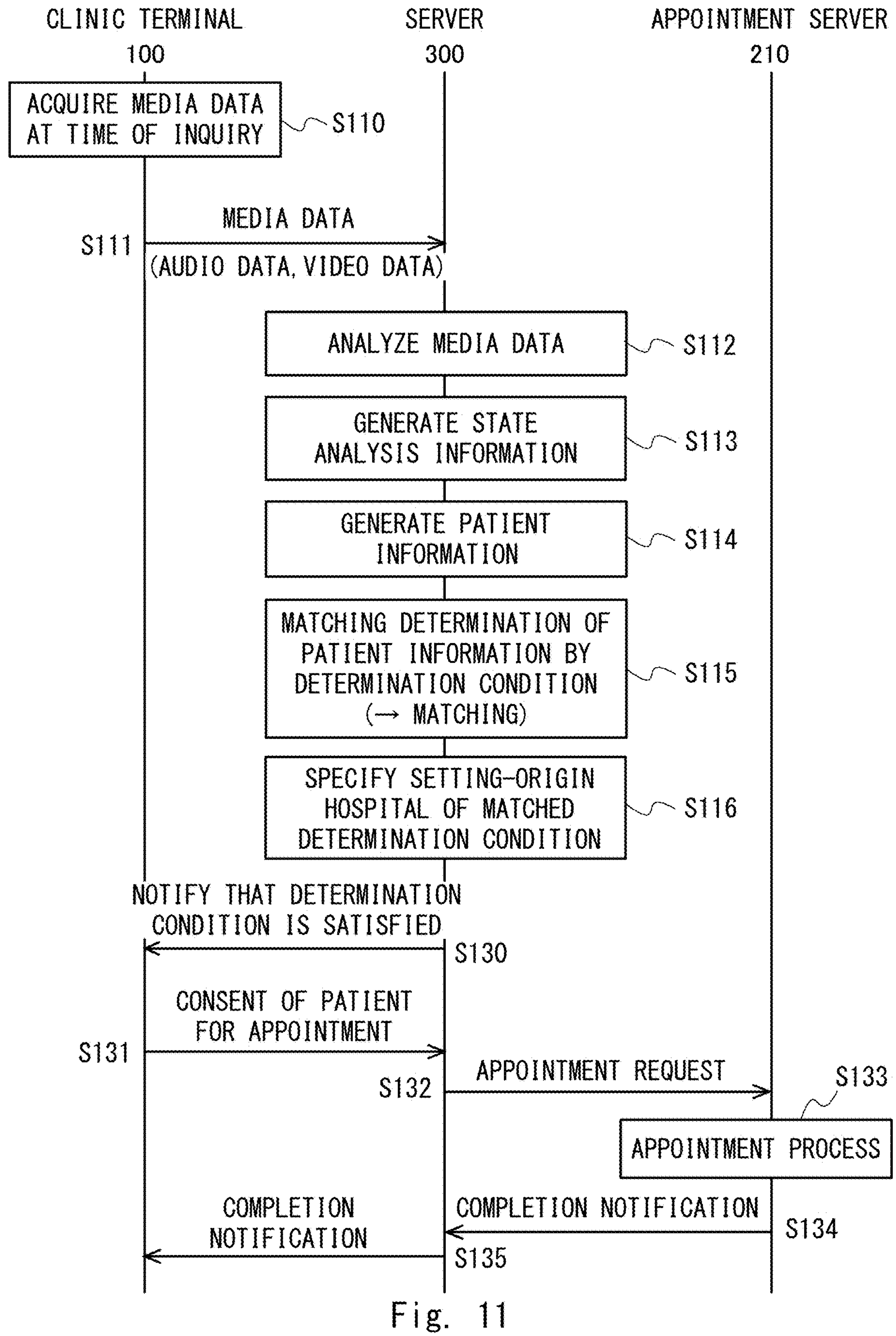
FIG. 11 is a sequence diagram showing a flow of a matching process according to a second modified example of the second example embodiment.

FIG. 11 is a sequence diagram showing a flow of a matching process according to the second modified example of the second example embodiment. The steps shown in FIG. 9 include steps S130 to S135 instead of the steps S117 and S118 shown in FIG. 7.

In the step S130, the processing control unit 306*a* of the server 300 notifies the clinic terminal 100 that the patient information of the target patient satisfies a determination condition. Setting-origin hospital information may be included in this notification. The clinic terminal 100 notifies the server 300 to that effect when the consent from the target patient for the appointment is obtained (S131). Note that the clinic terminal 100 may transmit information about a candidate date for the appointment requested by the target patient to the server 300. Next, the processing control unit 306*a* of the server 300 transmits an appointment request for a medical consultation of examination to the appointment server 210 of the second institution (S132). The name of a doctor of the setting-origin hospital terminal 200, a clinical department, and the candidate date for the appointment may be included in the appointment request. The appointment server 210 performs an appointment process based on the appointment request (S133). Then, when the appointment process is completed, the appointment server 210 transmits a completion notification to the clinic terminal 100 through the server 300 (S134 and S135).

Note that instead of performing the processes in the steps S131 to S133, the clinic terminal 100 may directly transmit the appointment request to the appointment server 210. In this case, the clinic terminal 100 may transmit the appointment request to the appointment server 210 when the consent from the target patient for the appointment is obtained.

Figure 12:
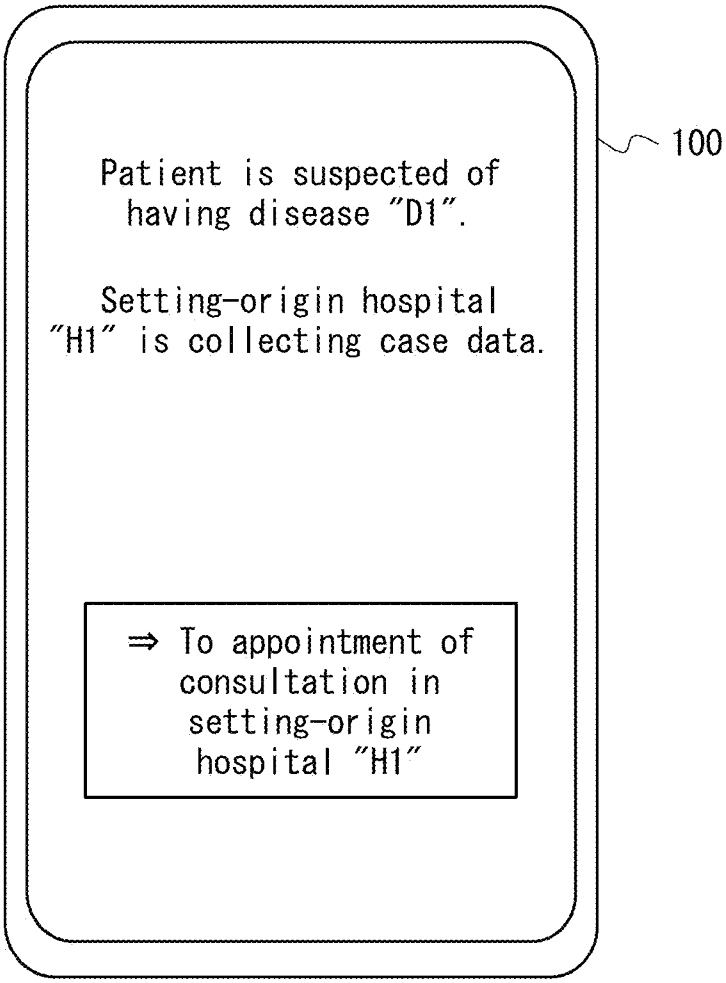
FIG. 12 shows an example of an image displayed on a clinic terminal according to the second modified example of the second example embodiment.

FIG. 12 shows an example of an image displayed on the clinic terminal 100 according to the second modified example of the second example embodiment. The fact that the target patient is suspected of having a disease "D1", and that a setting-origin hospital "H1" is collecting case data is displayed on the display unit of the clinic terminal 100 which has received the notification in the step S130. Further, an operation area for making an appointment for a medical consultation or examination at the setting-origin hospital "H1" may be displayed on the display unit of the clinic terminal 100. The person associated with the clinic accesses an appointment site by operating this operation area, and transmits an appointment request to the appointment server 210 when he/she obtains the consent from the target patient.

Third Modified Example of Second Example Embodiment

In the above description, the determination unit 305*a* determines that a determination condition is satisfied when all the individual determination conditions constituting the same determination condition are satisfied. Note that the information acquisition unit 303*a* of the server 300 may acquire media data of a patient at predetermined intervals, and the analysis unit 304 may generate patient information in response to the acquisition of the media data. Then, in response to the generation of the patient information, the determination unit 305*a* may successively determine whether or not each of the individual determination conditions matches. When the patient information matches with an individual determination condition for determining a certain state included in a certain determination condition, the determination unit 305*a* may transmit question information for determining individual determination conditions for remaining states to the clinic terminal 100. Then, the determination unit 305*a* may cause the clinic terminal 100 to output the question information.

For example, it is assumed that the target patient is questioned by a doctor using the clinic terminal 100, and the fact that the target patient has symptoms of "dizziness" and "stomachache" is detected by the server 300. The symptoms of "dizziness" and "stomachache" satisfy the first and second individual determination conditions included in the determination condition "C3". In this case, in order to ask the target patient a question about the remaining third individual determination condition, which is also included in the determination condition "C3", the clinic terminal 100 is made to output a question "Do you have any hearing loss?". In this way, it is possible to, by shortening the interval at which media data are acquired and the interval at which other processes are performed, ask the target patient a question about the remaining individual determination condition in real time.

Note that the determination unit 305*a* may cause, when a ratio of the number of individual determination conditions that have already matched to the number of all the individual determination conditions constituting the same determination condition reaches or exceeds a predetermined ratio, the clinic terminal 100 to output question information about the remaining individual determination conditions of this determination condition.

Figure 13:
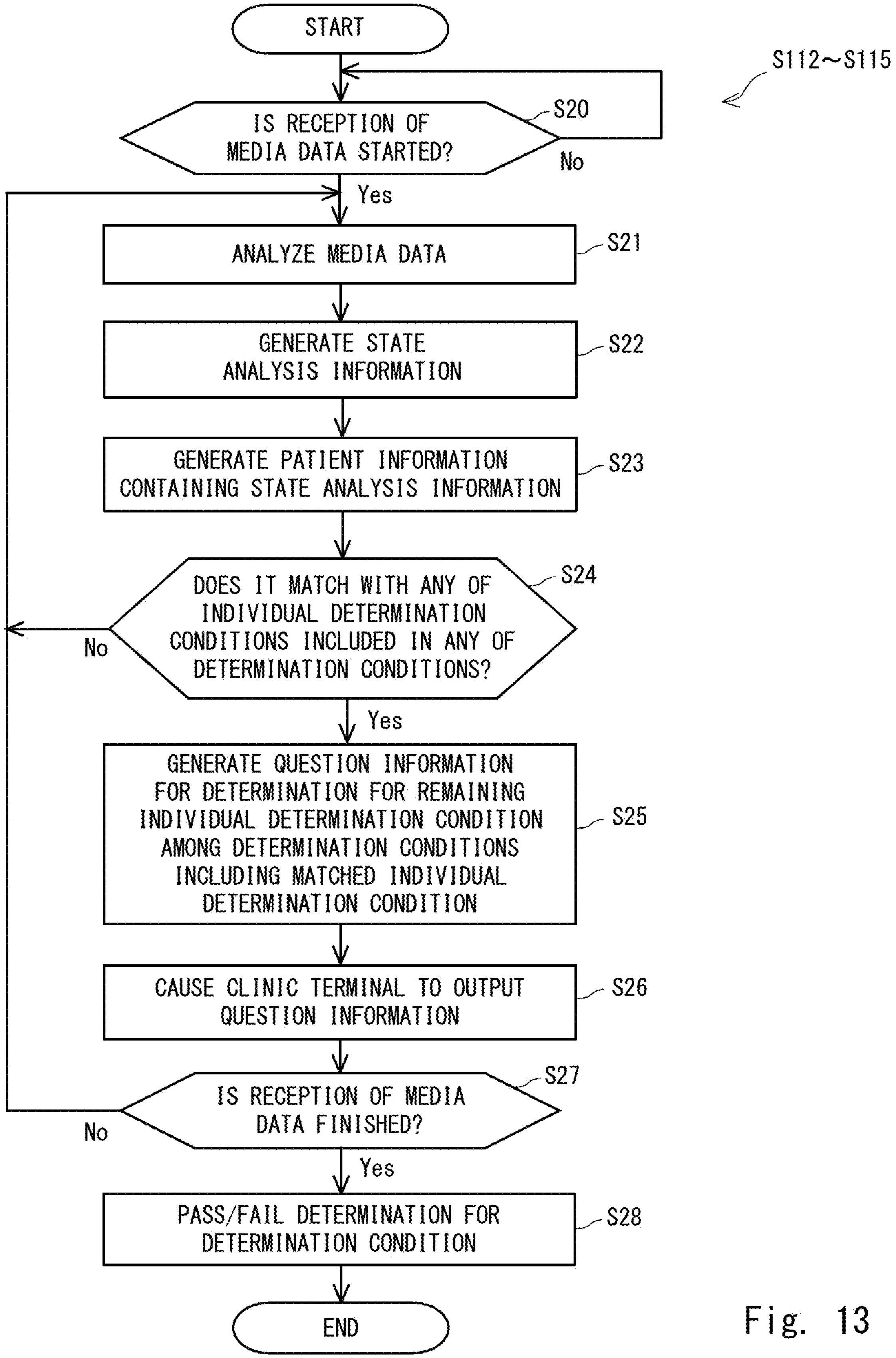
FIG. 13 is a flowchart showing an example of a flow of analysis and determination processes according to a third modified example of the second example embodiment.

FIG. 13 is a flowchart showing an example of a flow of analysis and determination processes according to a third modified example of the second example embodiment. The analysis process corresponds to the steps S112 to S114 shown in FIGS. 7, 9 and 11, and the determination process corresponds to the step S115 shown in FIGS. 7, 9 and 11.

Firstly, when the information acquisition unit 303*a* of the server 300 starts receiving media data of a target patient (Yes in S20), the analysis unit 304 analyzes the received media data (S21). Then, the analysis unit 304 generates state analysis information based on the media data (S22) and generates patient information containing the state analysis information (S23).

Next, the determination unit 305*a* determines whether or not the patient information of the target patient satisfies any of individual determination conditions included in any of determination conditions (S24). When the patient information of the target patient does not satisfy any individual determination condition (No in S24), the determination unit 305*a* returns the process to the step S21. On the other hand, when the patient information of the target patient satisfies at least one individual determination condition (Yes in S24), the determination unit 305*a* advances the process to a step S25.

In the step S25, the determination unit 305*a* generates question information for a determination for an undetermined individual determination condition included in the determination condition including the matched individual determination condition (Step S25). Next, the determination unit 305*a* causes the clinic terminal 100 to output the question information (Step S26).

The server 300 repeats the steps S21 to S26 until the information acquisition unit 303*a* finishes the reception of the media data. Then, when the information acquisition unit 303*a* has finished the reception of media data (Yes in S27), the server 300 makes a pass/fail determination as to whether or not there is a determination condition of which all the individual determination conditions have matched based on the results of the determinations that have been made so far (S28). Then, the server 300 finishes the analysis and determination processes.

As described above, the server 300 causes the clinic terminal 100 to ask the patient a question according to the determination result of individual determination conditions, whereby it is possible to, even if the doctor of the clinic does not have knowledge about the content of the designated determination conditions, acquire patient information based on which the determination is made without omission.

Third Example Embodiment

Next, a third example embodiment according to the present disclosure will be described. In the second example embodiment, the determination unit 305*a* carries out a determination process by using a determination condition for determining whether or not there is a specific state or for determining whether a specific state is within a reference range. In contrast, in the third example embodiment, the determination unit 305*a* determines that a determination condition is satisfied when a specific state of a target patient is similar to that of a reference patient. That is, the determination condition includes a closeness determination condition based on closeness of the state of a target patient to that of a reference patient. The reference patient is a patient who was diagnosed by a doctor of a setting-origin hospital as being suspected of having a certain disease in the past. For example, the closeness determination condition is a condition for determining whether or not a value indicating closeness of patient information of the target patient to that of the reference patient is smaller than a predetermined threshold. In this case, the patient information may be feature amounts or a feature vector indicating a state related to a predetermined determination provision. The feature amounts or the feature vector may be extracted from media data.

Figure 14:
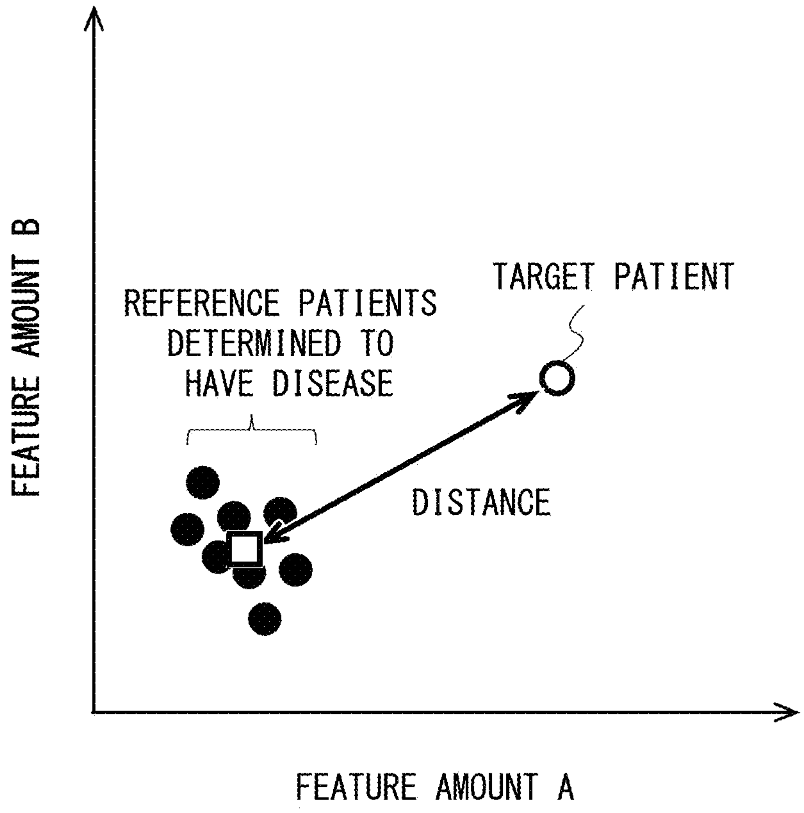
FIG. 14 is a diagram for explaining a determination process according to a third example embodiment.

FIG. 14 is a diagram for explaining a determination process according to the third example embodiment. The determination process corresponds to the step S115 shown in FIGS. 7, 9 and 11. FIG. 14 shows a space in which feature vectors each having feature amounts A and B as its elements are expressed. For example, the feature amounts A and B are extracted from video data as feature amounts indicating a state level of a predetermined determination provision. Each of black circles (●) in this drawing indicates a feature vector composed of feature amounts extracted from video data of a respective reference patient who was diagnosed as having a disease. Further, a white circle (○) indicates a feature vector composed of feature amounts extracted from video data of the target patient. For example, the determination unit 305*a* calculates the distance between the white circle and a black circle and determines whether the distance is shorter than a predetermined threshold. Note that the determination unit 305*a* may calculate the distance between the white circle and a black circle by using a well-known method such as a group average method or a Ward's method.

Note that what kind of feature amounts are extracted to generate a feature vector is determined for each determination condition. Further, the threshold for the closeness may be a constant value irrespective of the determination condition or may be determined for each determination condition. For example, the determination unit 305*a* determines that a given determination condition is satisfied when the distance calculated by using a feature vector determined for this determination condition is shorter than a threshold determined for this determination condition.

Figure 15:
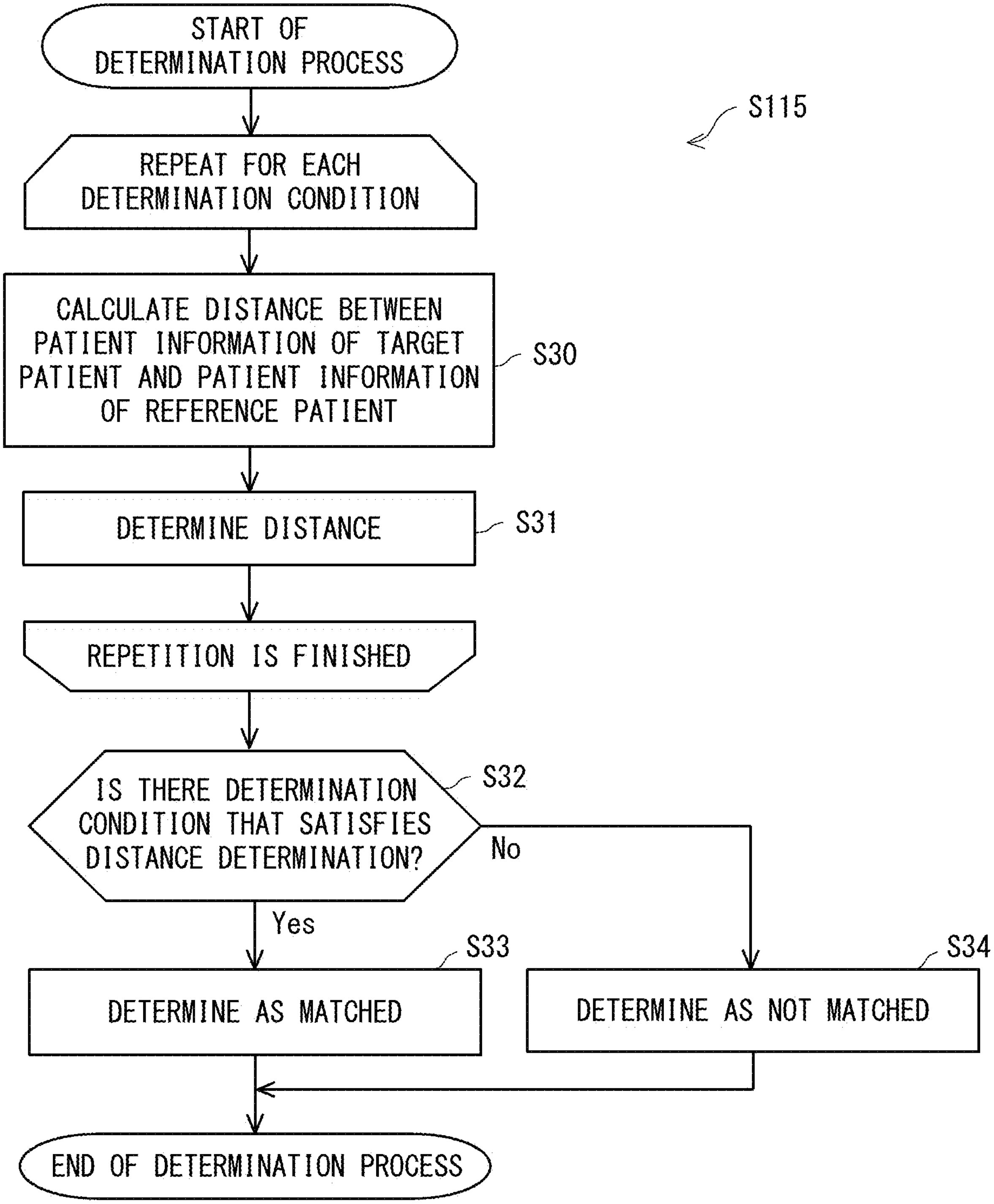
FIG. 15 is a flowchart showing an example of a flow of a determination process according to the third example embodiment.

FIG. 15 is a flowchart showing an example of a flow of a determination process according to the third example embodiment. Firstly, the determination unit 305*a* of the server 300 repeats processes shown in steps S30 and S31 for each of determination conditions registered in the determination condition DB 302. In the step S30, the determination unit 305*a* of the server 300 calculates the distance between patient information of the target patient and patient information of the reference patient based on the determination condition. Next, in the step S31, the determination unit 305*a* determines whether or not the distance is shorter than a threshold under the aforementioned determination condition.

Next, in the step S32, the determination unit 305*a* determines whether there is a determination condition that satisfies the distance determination. When there is a determination condition that satisfies the distance determination (Yes in Step S32), the determination unit 305*a* determines that the determination condition matches (S33). On the other hand, when there is no determination condition that satisfies the distance determination (No in Step S32), the determination unit 305*a* determines that no determination condition matches (S34). Then, the determination unit 305*a* finishes the determination process.

As described above, according to the third example embodiment, the server 300 determines that a determination condition is satisfied when a specific state of a target patient is similar to that of a reference patient, and therefore can take a small change in the target patient into consideration in the determination process. Therefore, the accuracy of the determination is improved.

Fourth Example Embodiment

Next, a fourth example embodiment according to the present disclosure will be described. In the above-described second and third example embodiments, the server 300 performs a matching process when patient information containing state analysis information based on media data satisfies a determination condition. Note that there are cases where a doctor of a clinic or a setting-origin hospital wants to examine the validity of a determination result by checking the media data based on which the determination result is obtained. Therefore, in the fourth example embodiment, a server 300*b* generates a summary of media data and transmits the generated summary to the clinic terminal 100 or the setting-origin hospital terminal 200.

Figure 16:
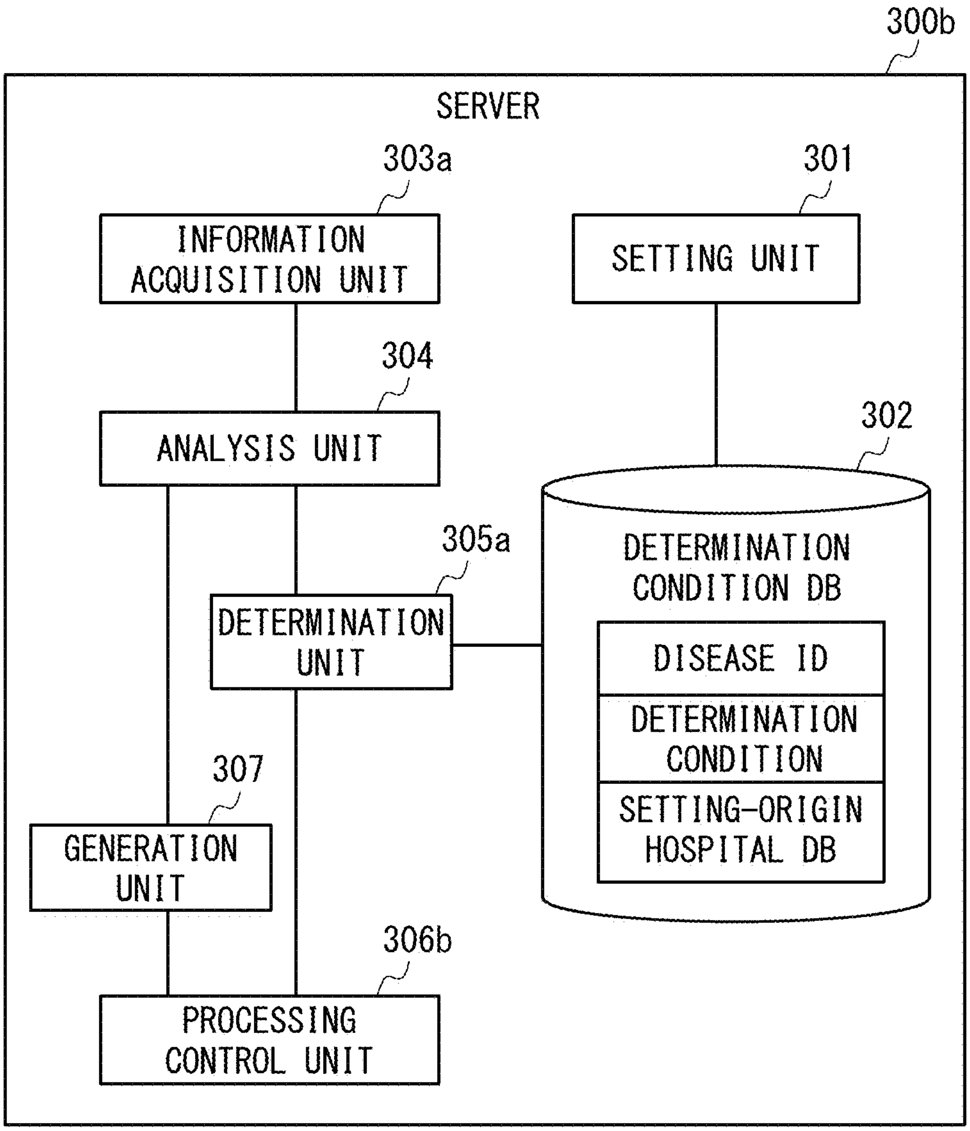
FIG. 16 is a block diagram showing a configuration of a server according to a fourth example embodiment.

FIG. 16 is a block diagram showing a configuration of the server 300*b* according to the fourth example embodiment. The server 300*b* includes a generation unit 307 and a processing control unit 306*b* in place of the processing control unit 306*a* of the above-described server 300.

The generation unit 307 is also referred to as generation means. The generation unit 307 generates summary data that are obtained by cutting out a part(s) related to state analysis information from audio data or video data. For example, the generation unit 307 may cut out a part(s) that was used to generate state analysis information from audio data or video data. Further, the generation unit 307 may use, as summary data, a remaining part of audio data or video data after deleting a part in which nobody speaks, a part in which there is no movement, or a part of which a relationship with the state is smaller than a predetermined threshold. Alternatively, the generation unit 307 may use, as summary data, a remaining part after deleting a part in which a redundant statement is made or a redundant movement is performed. Alternatively, the generation unit 307 may generate summary data by editing media data so that a statement or a movement highly related to the state is emphasized. For example, as a method for emphasizing a statement or a movement, the generation unit 307 may increase the volume for a statement of which relevance to the state is equal to or larger than a predetermined threshold, or may magnify a movement area for a scene in which relevance to the state is equal to or larger than a predetermined threshold.

When at least one determination condition is satisfied, the processing control unit 306*b* transmits summary data to the clinic terminal 100 or the setting-origin hospital terminal 200. Then, the processing control unit 306*b* causes the clinic terminal 100 or the setting-origin hospital terminal 200 to output the summary data.

Figure 17:
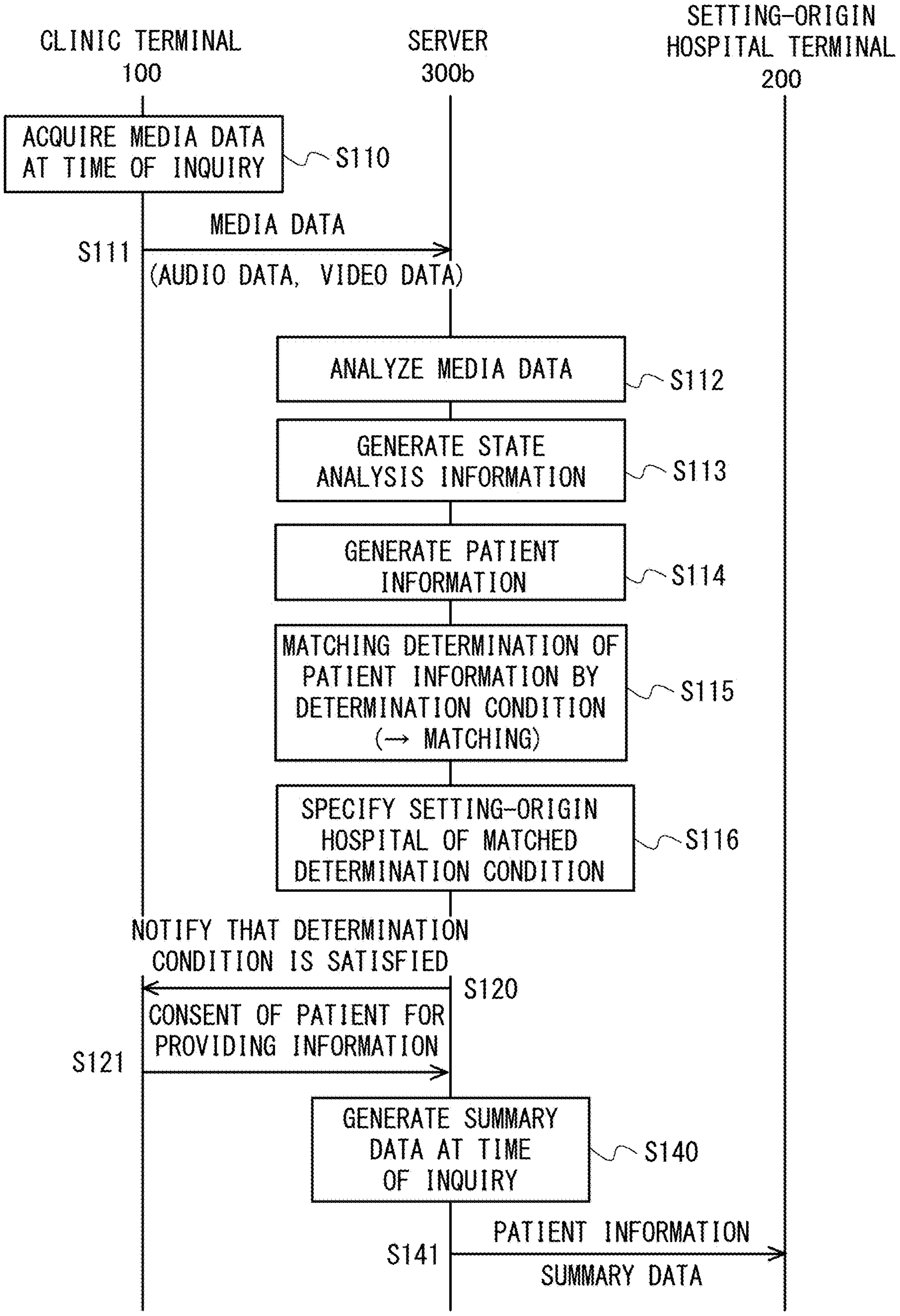
FIG. 17 is a sequence diagram showing a flow of a matching process according to the fourth example embodiment.

FIG. 17 is a sequence diagram showing a flow of a matching process according to the fourth example embodiment. The steps in FIG. 17 include steps S140 and S141 instead of the step S122 shown in FIG. 9.

Firstly, the information processing system 1*a* performs processes similar to those in the steps S110 to S116 and the steps S120 and S121 shown in FIG. 9. Next, the generation unit 307 of the server 300*b* generates summary data at the time of inquiry based on media data at the time of the inquiry (S140). Next, the processing control unit 306*b* of the server 300*b* transmits the generated summary data together with patient information to the setting-origin hospital terminal 200 (S141). By having the setting-origin hospital terminal 200 output the summary data, the doctor at the setting-origin hospital terminal 200 can easily examine the validity of the determination result before actually examining the target patient.

Note that the process shown in the step S140 may be performed in parallel with the analysis process and the determination process, or may be performed according to the fact that a matching determination is made in the step S115.

Fifth Example Embodiment

Next, a fifth example embodiment according to the present disclosure will be described. In the second to fourth example embodiments, the video data are obtained by photographing (or filming) the target patient who visited the clinic by the camera 110 provided in the clinic, and the audio data are obtained by collecting voices of the target patient who visited the clinic by the microphone 120. In contrast, a target patient receives online medicine (e.g., online consultation or examination) in the fifth example embodiment. Therefore, in the fifth example embodiment, the video data are one that is obtained by photographing (or filming) the target patient who is in a remote facility such as his/her home or a simplified clinic (e.g., a mobile clinic), and the audio data are one that is obtained by collecting voices of the target patient who is in the remote facility.

Figure 18:
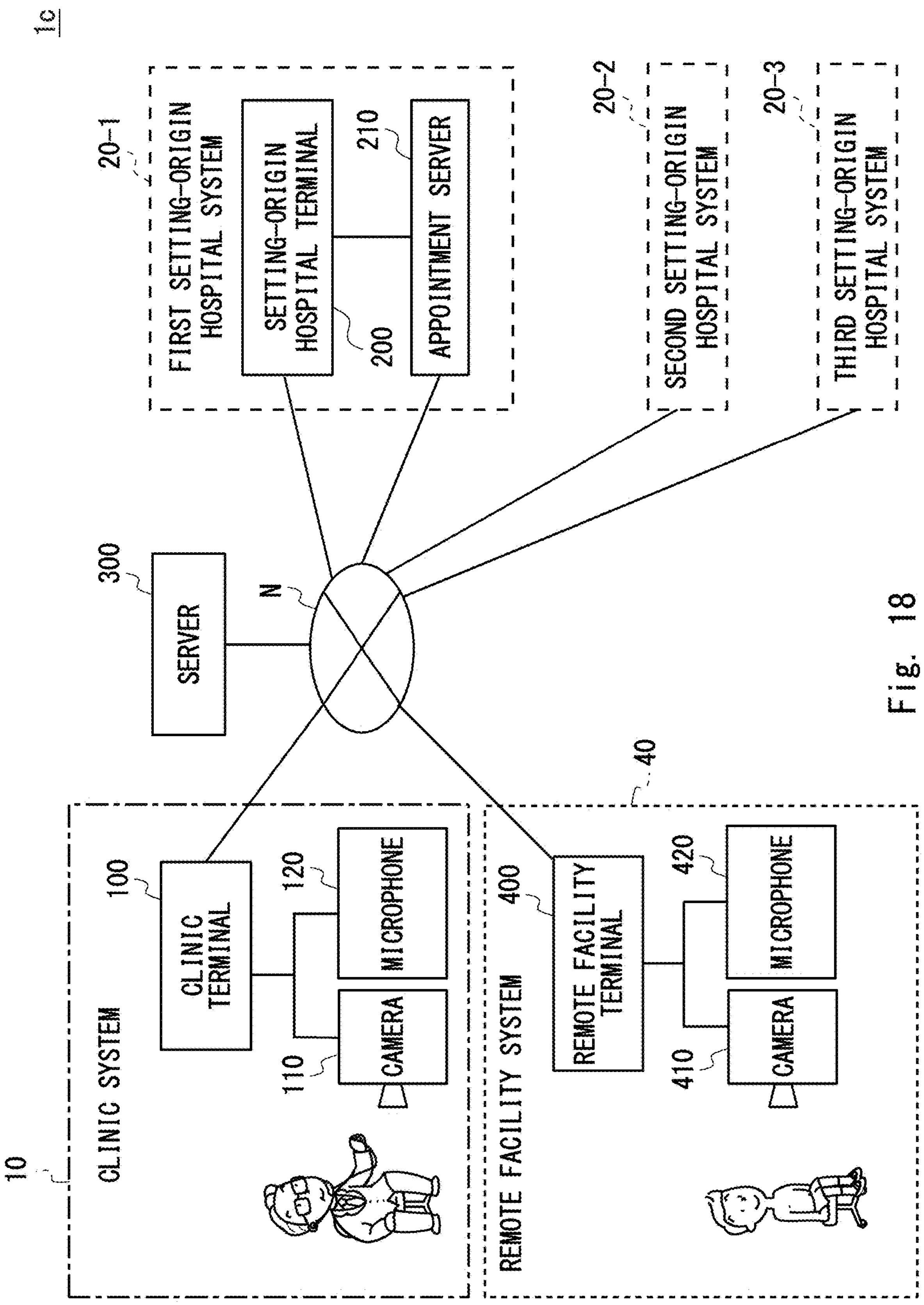
FIG. 18 is a block diagram showing an overall configuration of an information processing system according to a fifth example embodiment.

FIG. 18 is a block diagram showing an overall configuration of an information processing system 1*c* according to the fifth example embodiment. The information processing system 1*c* includes a remote facility system 40 in addition to the components/structures of the information processing system 1*a*.

The remote facility system 40 is a computer system provided in a remote facility where the target patient is present. The remote facility system 40 includes a remote facility terminal 400, a camera 410, and a microphone 420. The camera 410 and the microphone 420 are provided in the remote facility of the target patient. The camera 410 photographs (films) the target patient present in the remote facility, and the microphone 420 collects voices of the target patient present in the remote facility. Then, the camera 410 and the microphone 420 transmit video data and audio data, respectively, to the remote facility terminal 400.

The remote facility terminal 400 is an information terminal provided in the remote facility or an information terminal managed by a person associated with the remote facility. The remote facility terminal 400 may be a personal computer, a smartphone, or a tablet-type terminal used by the user. Further, the remote facility terminal 400 transmits media data acquired from the camera 410 and the microphone 420 to the clinic terminal 100 through the network N. Further, the remote facility terminal 400 receives video data taken by the camera 110 and audio data collected by the microphone 120 from the clinic system 10 through the network N. In this way, the doctor of the clinic can check the appearance of the target patient and examine the target patient. Note that the camera 110 of the clinic system 10 is not indispensable.

The remote facility terminal 400 also transmits media data acquired from the camera 410 and the microphone 420 to the server 300 through the network N.

Then, the analysis unit 304 of the server 300 analyzes the media data acquired from the camera 410 and the microphone 420 through the remote facility terminal 400 and generates state analysis information and patient information. Note that the analysis unit 304 of the server 300 may also include the media data acquired from the camera 110 and the microphone 120 through the clinic terminal 100 in the information based on which the analysis is made.

As described above, according to the fifth example embodiment, effects similar to those obtained in the second to fourth example embodiments can be obtained even when the patient receives online medicine.

Note that the above-described example embodiments have been described as hardware configurations, but the present disclosure is not limited to the hardware configurations. The present disclosure may also be implemented by causing a CPU to execute a computer program.

Figure 19:
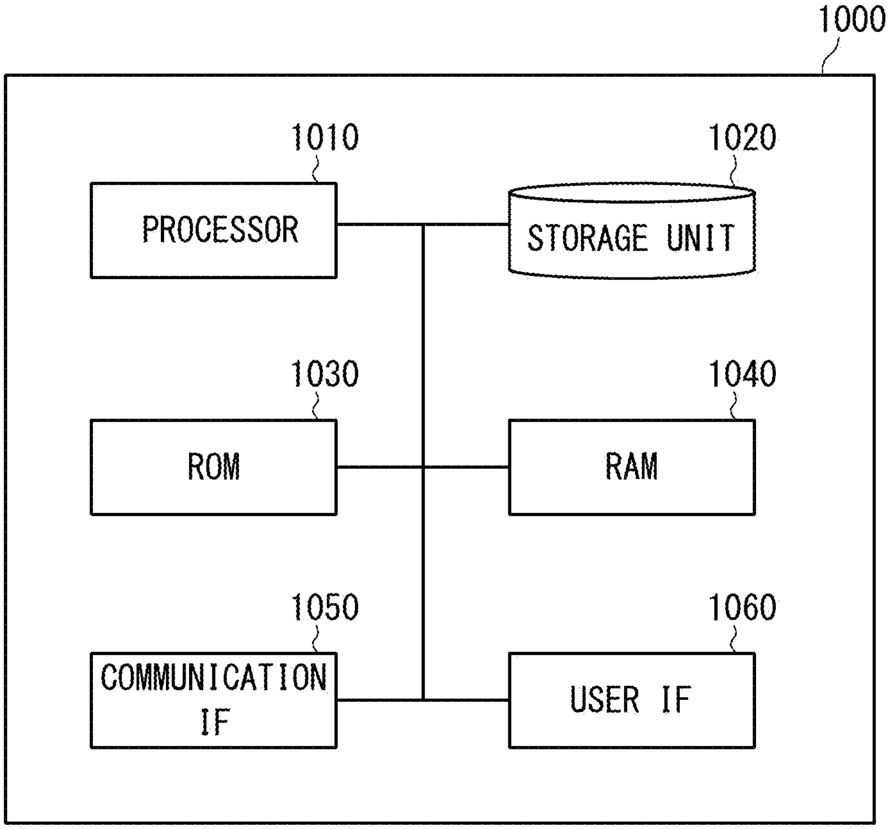
FIG. 19 shows an example of a configuration of a computer.

FIG. 19 shows an example of a configuration of a computer used as the clinic terminal 100, the setting-origin hospital terminal 200, the appointment server 210, the server 300, or the server 300*b*. The computer apparatus 1000 includes a processor 1010, a storage unit 1020, a ROM (Read Only Memory) 1030, a RAM (Random Access Memory) 1040, a communication interface (IF: Interface) 1050, and a user interface 1060.

The communication interface 1050 is an interface for connecting the computer apparatus 1000 to a communication network through wired communication means, wireless communication means, or the like. The user interface 1060 includes, for example, a display unit such as a display. Further, the user interface 1060 includes an input unit such as a keyboard, a mouse, and a touch panel. Note that the user interface 1060 is not indispensable.

The storage unit 1020 is an auxiliary storage device that can hold various types of data. The storage unit 1020 does not necessarily have to be a part of the computer apparatus 1000, but may be an external storage device, or a cloud storage connected to the computer apparatus 1000 through a network.

The ROM 1030 is a non-volatile storage device. For example, a semiconductor storage device such as a flash memory having a relatively small capacity can be used for the ROM 1030. A program(s) that is executed by the CPU 1010 may be stored in the storage unit 1020 or the ROM 1030. The storage unit 1020 or the ROM 1030 stores, for example, various programs for implementing the function of each unit in the server.

In the above-described examples, the program includes a set of instructions (or software codes) that, when read into a computer, causes the computer to perform one or more of the functions described in the example embodiments. The program may be stored in a non-transitory computer readable medium or in a physical storage medium. By way of example rather than limitation, a computer readable medium or a physical storage medium may include a random-access memory (RAM), a read-only memory (ROM), a flash memory, a solid-state drive (SSD), or other memory technology, a CD-ROM, a digital versatile disc (DVD), a Blu-ray (registered trademark) disc or other optical disc storages, a magnetic cassette, magnetic tape, and a magnetic disc storage or other magnetic storage devices. The program may be transmitted on a transitory computer readable medium or a communication medium. By way of example rather than limitation, the transitory computer readable medium or the communication medium may include electrical, optical, acoustic, or other forms of propagating signals.

The RAM 1040 is a volatile storage device. As the RAM 1040, various types of semiconductor memory apparatuses such as a DRAM (Dynamic Random Access Memory) or an SRAM (Static Random Access Memory) can be used. The RAM 1040 can be used as an internal buffer for temporarily storing data and the like. The CPU 1010 expands (i.e., loads) a program stored in the storage unit 1020 or the ROM 1030 in the RAM 1040, and executes the expanded (i.e., loaded) program. The processor 1010 may be a CPU (Central Processing Unit) or a GPU (Graphics Processing Unit). When the processor 1010 performs a program, the functions of each unit in the server may be realized. The processor 1010 may include an internal buffer in which data or the like can be temporarily stored.

Note that the present disclosure is not limited to the above-described example embodiments, and they may be modified as appropriate without departing from the scope and spirit of the disclosure.

The whole or part of the example embodiments disclosed above can be described as, but not limited to, the following Supplementary notes.

(Supplementary Note 1)

An information processing system comprising:

information acquisition means for acquiring patient information indicating a state of a patient who has visited a first institution or who has been examined by a person associated with the first institution;

determination means for determining whether or not the patient information satisfies at least one of predetermined determination conditions; and processing control means for, when the patient information satisfies at least one of the determination conditions, performing a process for matching a second institution included in setting-origin institutions associated with the satisfied determination condition with the patient, wherein each of the predetermined determination conditions is a condition for determining whether a suspicion of a predetermined disease is correct or not, and is associated with a setting-origin institution that has set that determination condition.

(Supplementary Note 2)

The information processing system described in Supplementary note 1, wherein when the patient information satisfies at least one of the determination conditions, the processing control means notifies a terminal of the first institution of information about the second institution or transmits the patient information to a terminal of the second institution.

(Supplementary Note 3)

The information processing system described in Supplementary note 1 or 2, wherein when there is a plurality of setting-origin institutions associated with the satisfied determination condition, the processing control means selects the second institution from among the plurality of setting-origin institutions based on registration information related to at least one of the patient, the first institution, and the setting-origin institution.

(Supplementary Note 4)

The information processing system described in any one of Supplementary notes 1 to 3, wherein the patient information contains state analysis information generated by analyzing the state of the patient based on audio data or video data of the patient at a time of inquiry made by the person associated with the first institution.

(Supplementary Note 5)

The information processing system described in Supplementary note 4, further comprising:

generation means for generating summary data that are obtained by cutting out a part related to the state analysis information from the audio data or the video data, wherein the processing control means transmits the summary data to a terminal of the first institution or a terminal of the second institution when the patient information satisfies at least one of the determination conditions.

(Supplementary Note 6)

The information processing system described in any one of Supplementary notes 1 to 5, wherein the patient information contains information described in a medical record.

(Supplementary Note 7)

The information processing system described in any one of Supplementary notes 1 to 6, wherein the determination conditions include a combination of individual determination conditions respectively related to a plurality of determination provisions, and when the patient information matches with at least one of the individual determination conditions related to some of the determination provisions of the determination condition, the determination unit causes the first institution to output question information for determining an individual determination condition related to the remaining determination provisions.

(Supplementary Note 8)

The information processing system described in any one of Supplementary notes 1 to 6, wherein the determination conditions include a closeness determination condition for determining whether or not a value indicating closeness of the patient information of the patient to that of a patient who was diagnosed to be suspected of having the predetermined disease in the past is smaller than a predetermined threshold.

(Supplementary Note 9)

The information processing system described in any one of Supplementary notes 1 to 8, further comprising:

setting means for registering, for each of the determination conditions, the determination condition in association with information about a setting-origin institution that has set the determination condition.

(Supplementary Note 10)

An information processing method comprising:

a process of acquiring patient information indicating a state of a patient who has visited a first institution or who has been examined by a person associated with the first institution;

a process of determining whether or not the patient information satisfies at least one of predetermined determination conditions; and a process of, when the patient information satisfies at least one of the determination conditions, performing a process for matching a second institution included in setting-origin institutions associated with the satisfied determination condition with the patient, wherein each of the predetermined determination conditions is a condition for determining whether a suspicion of a predetermined disease is correct or not, and is associated with a setting-origin institution that has set that determination condition.

(Supplementary Note 11)

A non-transitory computer readable medium storing a program for causing a computer to perform:

a process of acquiring patient information indicating a state of a patient who has visited a first institution or who has been examined by a person associated with the first institution;

a process of determining whether or not the patient information satisfies at least one of predetermined determination conditions; and a process of, when the patient information satisfies at least one of the determination conditions, performing a process for matching a second institution included in setting-origin institutions associated with the satisfied determination condition with the patient, wherein each of the predetermined determination conditions is a condition for determining whether a suspicion of a predetermined disease is correct or not, and is associated with a setting-origin institution that has set that determination condition.

REFERENCE SIGNS LIST

1, 1*a* INFORMATION PROCESSING SYSTEM
10 CLINIC SYSTEM
20 SETTING-ORIGIN HOSPITAL SYSTEM
40 REMOTE FACILITY SYSTEM
100 CLINIC TERMINAL
110 CAMERA
120 MICROPHONE
200 SETTING-ORIGIN HOSPITAL TERMINAL
210 APPOINTMENT SERVER
300, 300*b* INFORMATION PROCESSING APPARATUS (SERVER)
301 SETTING UNIT
302 DETERMINATION CONDITION DB
303, 303*a* INFORMATION ACQUISITION UNIT
304 ANALYSIS UNIT
305, 305*a* DETERMINATION UNIT
306, 306*a*, 306*b* PROCESSING CONTROL UNIT
307 GENERATION UNIT
400 REMOTE FACILITY TERMINAL
410 CAMERA
420 MICROPHONE
1000 COMPUTER
1010 PROCESSOR
1020 STORAGE UNIT
1030 ROM
1040 RAM
1050 COMMUNICATION INTERFACE
1060 USER INTERFACE
N NETWORK

What is claimed is:

1. An information processing system comprising:

at least one memory storing instructions; and at least one processor configured to execute the instructions to:

acquire patient information indicating a state of a patient who has visited a first institution or who has been examined by a person associated with the first institution;

determine whether or not the patient information satisfies at least one of predetermined determination conditions; and perform, when the patient information satisfies at least one of the determination conditions, a process for matching a second institution included in setting-origin institutions associated with the satisfied determination condition with the patient, wherein each of the predetermined determination conditions is a condition for the patient information set by the setting-origin institutions for determining whether a predetermined disease is suspected or not, and is associated with the setting-origin institution that has set that determination condition, the state of the patient indicated in the patient information indicates whether there is a symptom associated with a disease, or a degree of morbidity of the symptom, the determination conditions include a closeness determination condition for determining whether or not a value indicating closeness of the patient information of the patient to that of a patient who was diagnosed to be suspected of having the predetermined disease in the past is smaller than a predetermined threshold, and the closeness determination condition is satisfied when a distance calculated using a feature vector of the patient information is shorter than the predetermined threshold.

2. The information processing system according to claim 1, wherein when the patient information satisfies at least one of the determination conditions, the at least one processor is further configured to execute the instructions to notify a terminal of the first institution of information about the second institution or transmit the patient information to a terminal of the second institution.

3. The information processing system according to claim 1, wherein when there is a plurality of setting-origin institutions associated with the satisfied determination condition, the at least one processor is further configured to execute the instructions to select the second institution from among the plurality of setting-origin institutions based on registration information related to at least one of the patient, the first institution, and the setting-origin institution.

4. The information processing system according to claim 1, wherein the patient information contains state analysis information generated by analyzing the state of the patient based on audio data or video data of the patient at a time of inquiry made by the person associated with the first institution.

5. The information processing system according to claim 4, wherein the at least one processor is further configured to execute the instructions to:

generate summary data that are obtained by cutting out a part related to the state analysis information from the audio data or the video data; and transmit the summary data to a terminal of the first institution or a terminal of the second institution when the patient information satisfies at least one of the determination conditions.

6. The information processing system according to claim 1, wherein the patient information contains information described in a medical record.

7. The information processing system according to claim 1, wherein the determination conditions include a combination of individual determination conditions respectively related to a plurality of determination provisions, and the at least one processor is further configured to execute the instructions to cause, when the patient information matches with at least one of the individual determination conditions related to some of the determination provisions of the determination condition, the first institution to output question information for determining an individual determination condition related to the remaining determination provisions.

8. The information processing system according to claim 1, wherein the at least one processor is further configured to execute the instructions to:

register, for each of the determination conditions, the determination condition in association with information about a setting-origin institution that has set the determination condition.

9. An information processing method comprising:

acquiring patient information indicating a state of a patient who has visited a first institution or who has been examined by a person associated with the first institution;

determining whether or not the patient information satisfies at least one of predetermined determination conditions; and when the patient information satisfies at least one of the determination conditions, performing a process for matching a second institution included in setting-origin institutions associated with the satisfied determination condition with the patient, wherein each of the predetermined determination conditions is a condition for the patient information set by the setting-origin institutions for determining whether a predetermined disease is suspected or not, and is associated with the setting-origin institution that has set that determination condition, the state of the patient indicated in the patient information indicates whether there is a symptom associated with a disease, or a degree of morbidity of the symptom, the determination conditions include a closeness determination condition for determining whether or not a value indicating closeness of the patient information of the patient to that of a patient who was diagnosed to be suspected of having the predetermined disease in the past is smaller than a predetermined threshold, and the closeness determination condition is satisfied when a distance calculated using a feature vector of the patient information is shorter than the predetermined threshold.

10. A non-transitory computer readable medium storing a program for causing a computer to perform:

acquiring patient information indicating a state of a patient who has visited a first institution or who has been examined by a person associated with the first institution;

determining whether or not the patient information satisfies at least one of predetermined determination conditions; and when the patient information satisfies at least one of the determination conditions, performing a process for matching a second institution included in setting-origin institutions associated with the satisfied determination condition with the patient, wherein each of the predetermined determination conditions is a condition for the patient information set by the setting-origin institutions for determining whether a predetermined disease is suspected or not, and is associated with the setting-origin institution that has set that determination condition, the state of the patient indicated in the patient information indicates whether there is a symptom associated with a disease, or a degree of morbidity of the symptom, the determination conditions include a closeness determination condition for determining whether or not a value indicating closeness of the patient information of the patient to that of a patient who was diagnosed to be suspected of having the predetermined disease in the past is smaller than a predetermined threshold, and the closeness determination condition is satisfied when a distance calculated using a feature vector of the patient information is shorter than the predetermined threshold.

11. The information processing system according to claim 1, wherein the at least one processor is further configured to execute the instructions to:

notify the first institution that the patient has been matched with the second institution; and in response to an acceptance notification received from the first institution as a trigger, transmit the patient information to a terminal of the matched second institution for the patient, and dispatch reservation parameters to a scheduling server.

12. The information processing system according to claim 1, wherein the at least one processor is further configured to execute the instructions to extract the feature vector of the patient information from audio data or video data of the patient.

13. The information processing method according to claim 9, further comprising extracting the feature vector of the patient information from audio data or video data of the patient.

14. The non-transitory computer readable medium according to claim 10, wherein the program further causes the computer to perform extracting the feature vector of the patient information from audio data or video data of the patient.

* * * * *